(12) United States Patent
Yoshikawa et al.

(10) Patent No.: US 10,942,127 B2
(45) Date of Patent: Mar. 9, 2021

(54) METHOD FOR MEASURING CONCENTRATION OF TEST SUBSTANCE, AND DETECTION APPARATUS

(71) Applicant: OSAKA UNIVERSITY, Osaka (JP)

(72) Inventors: Hiroyuki Yoshikawa, Osaka (JP); Eiichi Tamiya, Osaka (JP); Shuhei Imura, Osaka (JP)

(73) Assignee: OSAKA UNIVERSITY, Osaka (JP)

(*) Notice: Subject to any disclaimer, the term of this patent is extended or adjusted under 35 U.S.C. 154(b) by 283 days.

(21) Appl. No.: 15/030,183

(22) PCT Filed: Oct. 20, 2014

(86) PCT No.: PCT/JP2014/077874
§ 371 (c)(1),
(2) Date: Jul. 12, 2016

(87) PCT Pub. No.: WO2015/060269
PCT Pub. Date: Apr. 30, 2015

(65) Prior Publication Data
US 2016/0305889 A1    Oct. 20, 2016

(30) Foreign Application Priority Data

Oct. 21, 2013  (JP) .............................. JP2013-218750
Oct. 22, 2013  (JP) .............................. JP2013-219688

(51) Int. Cl.
*C12Q 1/26*   (2006.01)
*G01N 21/17*  (2006.01)
(Continued)

(52) U.S. Cl.
CPC ............... *G01N 21/82* (2013.01); *C12Q 1/26* (2013.01); *G01N 21/17* (2013.01);
(Continued)

(58) Field of Classification Search
CPC ...... C12G 1/26; G01N 21/17; G01N 21/1717; G01N 2021/1725
See application file for complete search history.

(56) References Cited

U.S. PATENT DOCUMENTS 5,019,496 A   5/1991  Oster et al.
5,035,997 A   7/1991  Oster et al.
(Continued)

FOREIGN PATENT DOCUMENTS

EP   1 343 012   9/2003
JP   57-6361     1/1982
(Continued)

OTHER PUBLICATIONS

Yoshikawa, "A new methodology for optical biosensing with dropcasting fabrication of sensor chips and irradiation/detection of a single laser beam", RSC Advances, 2015, (5), 56423. (Year: 2015).*
(Continued)

*Primary Examiner* — Robert J Yamasaki
*Assistant Examiner* — Charles Zoltan Constantine
(74) *Attorney, Agent, or Firm* — Wenderoth, Lind & Ponack, L.L.P.

(57) ABSTRACT

The present invention provide a method for detecting a test substance utilizing a color development caused by an enzyme reaction, or a color development caused by a specific interaction such as an antigen-antibody reaction and an enzyme reaction, the test substance being detected rapidly, sensitively and quantitatively without using a spectroscopic measurement device. The method for measuring a concentration of a test substance by the present invention comprises the steps of: generating a peroxide from the test substance; obtaining a polymerized substance by bringing an oxidoreductase for producing a polymerized substance and a substrate of the oxidoreductase for producing a polymer-
(Continued)

ized substance into contact with the peroxide; and irradiating the polymerized substance with light to record a temporal variation information of an intensity of scattered light generated from an irradiation point.

4 Claims, 40 Drawing Sheets

(51) Int. Cl.
  *G01N 21/82* (2006.01)
  *G01N 33/58* (2006.01)
  *G01N 33/535* (2006.01)
  *G01N 21/78* (2006.01)
  *G01N 21/77* (2006.01)

(52) U.S. Cl.
  CPC ......... *G01N 21/1717* (2013.01); *G01N 21/78* (2013.01); *G01N 33/535* (2013.01); *G01N 33/581* (2013.01); *G01N 2021/1725* (2013.01); *G01N 2021/7773* (2013.01); *G01N 2201/062* (2013.01); *G01N 2201/06113* (2013.01); *G01N 2333/904* (2013.01)

(56) References Cited

U.S. PATENT DOCUMENTS

| | | | |
|---|---|---|---|
| 2005/0048599 | A1 | 3/2005 | Goldberg et al. |
| 2007/0037225 | A1 | 2/2007 | Metzger et al. |
| 2007/0211985 | A1 | 9/2007 | Duer |
| 2008/0227126 | A1 | 9/2008 | Uematsu et al. |
| 2008/0241858 | A1 | 10/2008 | Metzger et al. |
| 2009/0068668 | A1 | 3/2009 | Duer |
| 2010/0136570 | A1 | 6/2010 | Goldberg et al. |
| 2010/0302544 | A1 | 12/2010 | Duer |
| 2011/0249260 | A1 | 10/2011 | Duer |
| 2012/0077206 | A1 | 3/2012 | Metzger et al. |
| 2012/0231532 | A1 | 9/2012 | Duer |
| 2012/0244607 | A1 | 9/2012 | Iwamoto et al. |
| 2013/0071850 | A1 | 3/2013 | Duer |
| 2013/0217063 | A1 | 8/2013 | Metzger et al. |
| 2014/0178861 | A1 | 6/2014 | Duer |
| 2014/0323340 | A1 | 10/2014 | Goldberg et al. |
| 2014/0363823 | A1 | 12/2014 | Goldberg et al. |
| 2015/0226730 | A1 | 8/2015 | Iwamoto et al. |
| 2016/0033412 | A1 | 2/2016 | Tan et al. |

FOREIGN PATENT DOCUMENTS

| | | |
|---|---|---|
| JP | 2-259567 | 10/1990 |
| JP | 2-259568 | 10/1990 |
| JP | 2007-531863 | 11/2007 |
| JP | 2008-224524 | 9/2008 |
| JP | 2012-525595 | 10/2012 |
| JP | 2012-215515 | 11/2012 |

OTHER PUBLICATIONS

Hempen ("Liquid chromatographic/mass spectrometric investigation on the reaction products in the peroxidase catalyzed oxidation of o-phenylenediamine by hydrogen peroxide", Analytical Bioanalytical Chemistry, 2005, 382, 234-238 (Year: 2005).*

Chu (Studies of Affinity Constants of Hapten-Specific Monoclonal Antibodies Using an Antibody-Immobilized ELISA, Biotechnology Progress, 1995, 11, 352-356) (Year: 1995).*

Yoshikawa et al., "Development of novel nanobiophotonics technologies using focused laser beams," 7th Symposium on Biorelevant Chemistry CSJ, Sep. 27-29, 2013, with full English translation.

Liang et al. "A Sensitive Resonance Scattering Spectral Assay for the Determination of Trace $H_2O_2$ Based on the HRP Catalytic Reaction and Nanogold Aggregation", Journal of Fluorescence, vol. 18 No. 6, 2008, pp. 1035-1041.

Yoshikawa et al., "Single-Beam Optical Biosensing Based on Enzyme-Linked Laser Nanopolymerization of o-Phenylenediamine", Analytical Chemistry, vol. 84, 2012, pp. 9811-9817.

Yoshikawa et al., "Formation of polyaniline nanostructures by a focused laser beam and enzyme reaction," The $92^{nd}$ CSJ Spring Annual Meeting, Mar. 25, 2012, with English translation.

Yoshikawa et al., "Deposition of poly(phenylenediamine) nanostructures and detection of enzyme reactions by using a visible focused laser beam," Annual meeting on Photochemistry 2012, with English translation.

Imura et al., "Rapid and high sensitive detection of the oxidative enzyme reaction using the nano photopolymerization by a focused laser beam," The 60th JSAP Spring Meeting 2013 Proceedings, Mar. 28, 2013, with English translation.

Yoshikawa et al., "Single beam biosensing by using laser polymerization and enzyme reactions," The 93rd CSJ Spring Annual Meeting, Mar. 25, 2013, with English translation.

Yoshikawa et al., "Enzymatic Biosensing based on Laser Nanopolymeriazation of o-Phenylene," International Conference on Photochemistry (ICP2013), Jul. 21-28, 2013.

Yoshikawa et al., Single-Beam Optical Biosensing Using Laser Nanopolymerization and Enzyme Reactions, SPIE2013, Optics + Photonics, Aug. 24-29, 2013.

Yoshikawa et al., "Development of novel nanobiophotonics technologies using focused laser beams," 7th Symposium on Biorelevant Chemistry CSJ, Sep. 27-29, 2013, with English translation.

International Search Report dated Nov. 11, 2014 in International (PCT) Application No. PCT/JP2014/077874.

Notification of Reasons for Refusal dated Jun. 26, 2018 in Japanese Patent Application No. 2015-543849, with English Translation.

Notification of Reasons for Refusal dated Jan. 29, 2019 in corresponding Japanese Patent Application No. 2015-543849 with English translation.

* cited by examiner

[FIG. 1]
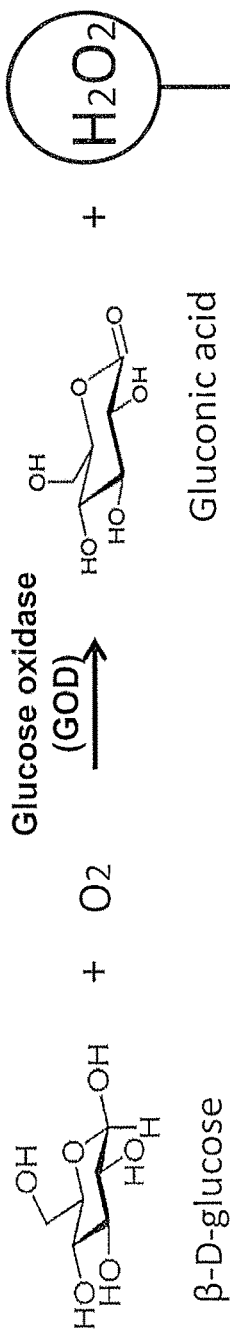

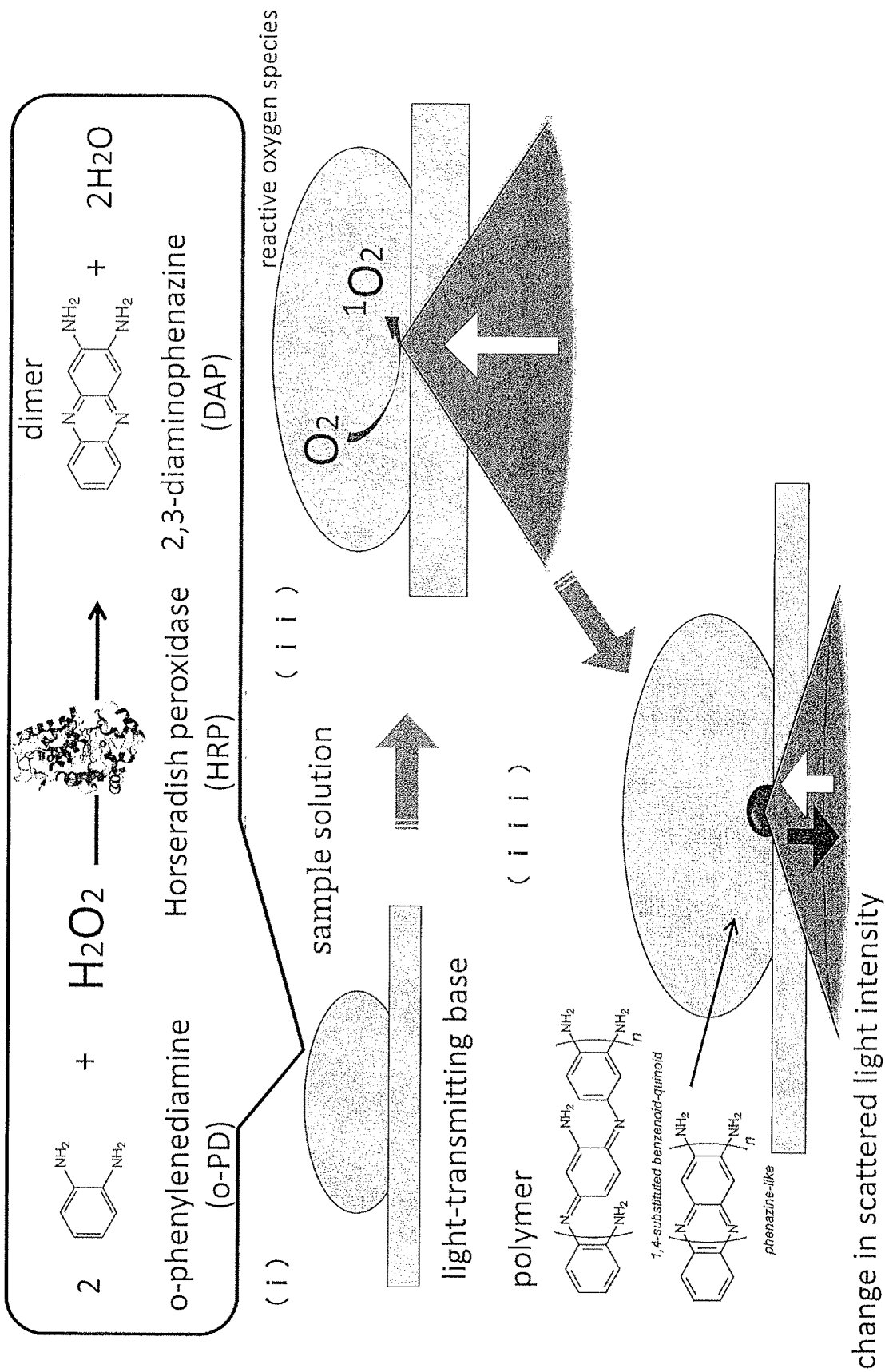
[FIG.2]

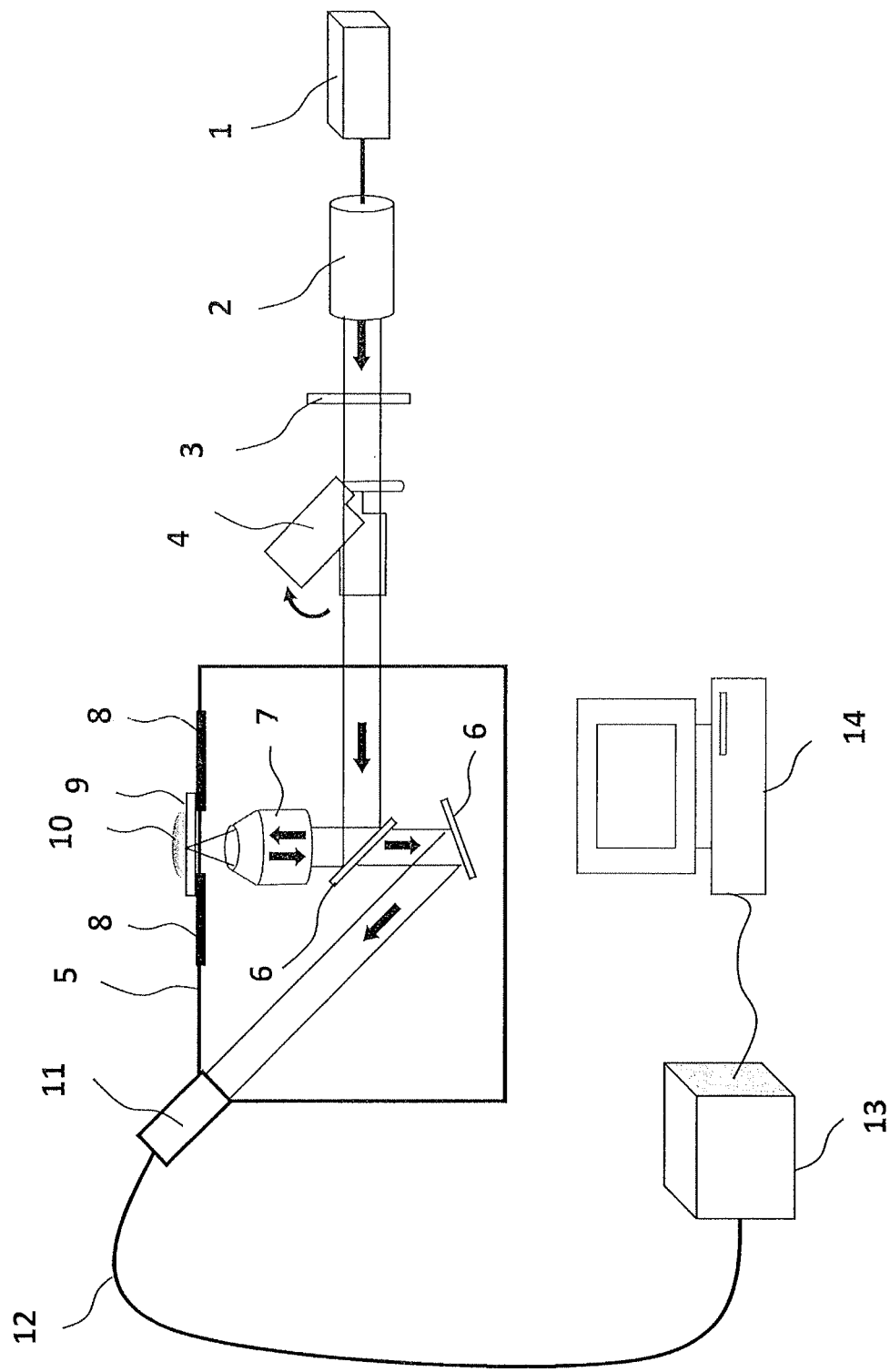
[FIG. 3]

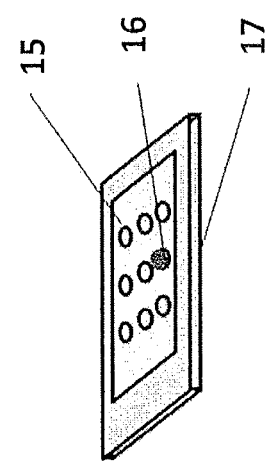
[FIG. 4]

[FIG. 5]
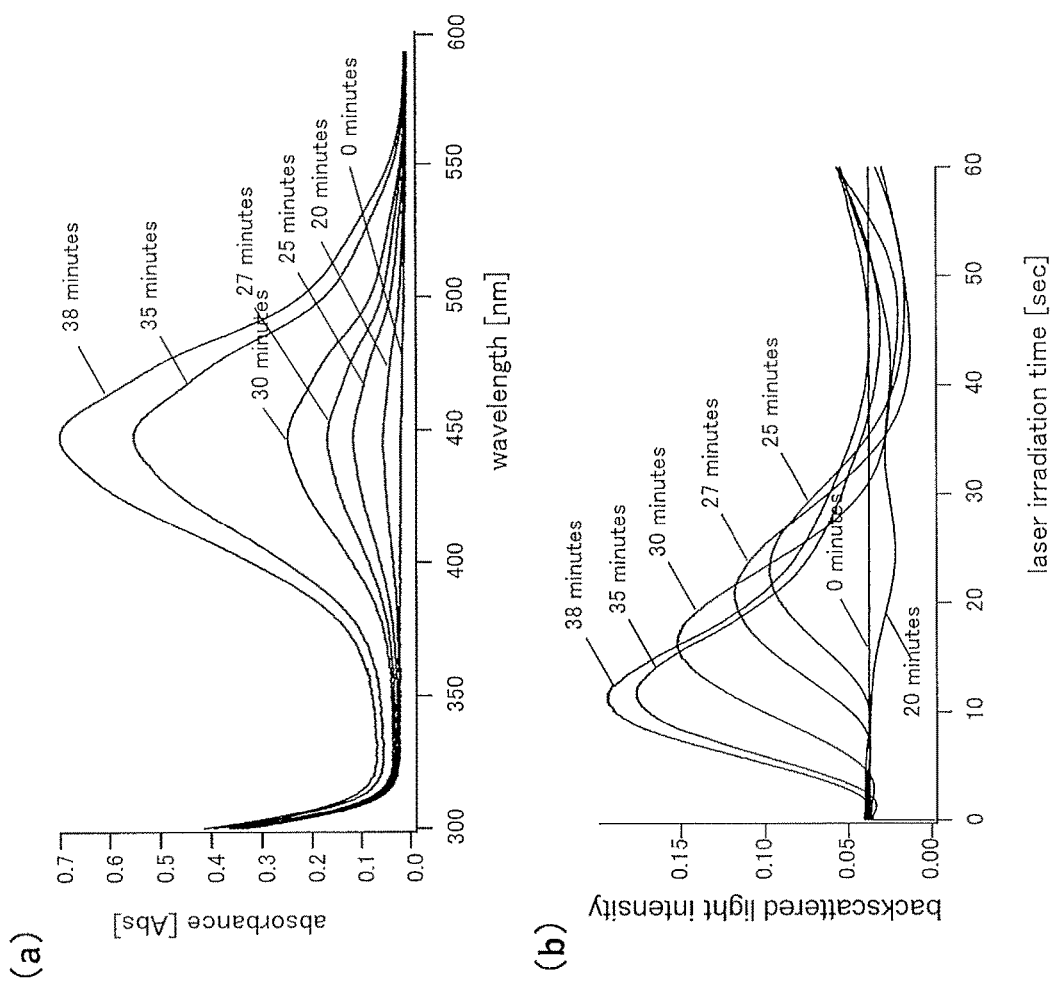

[FIG. 6]
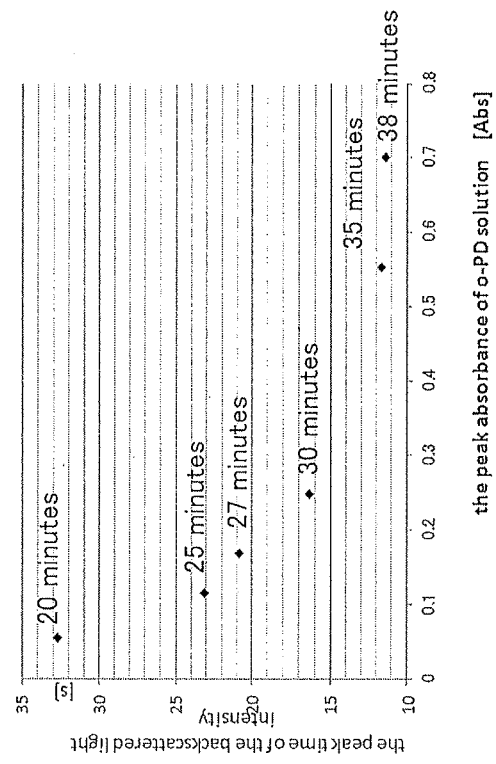

[FIG. 7]
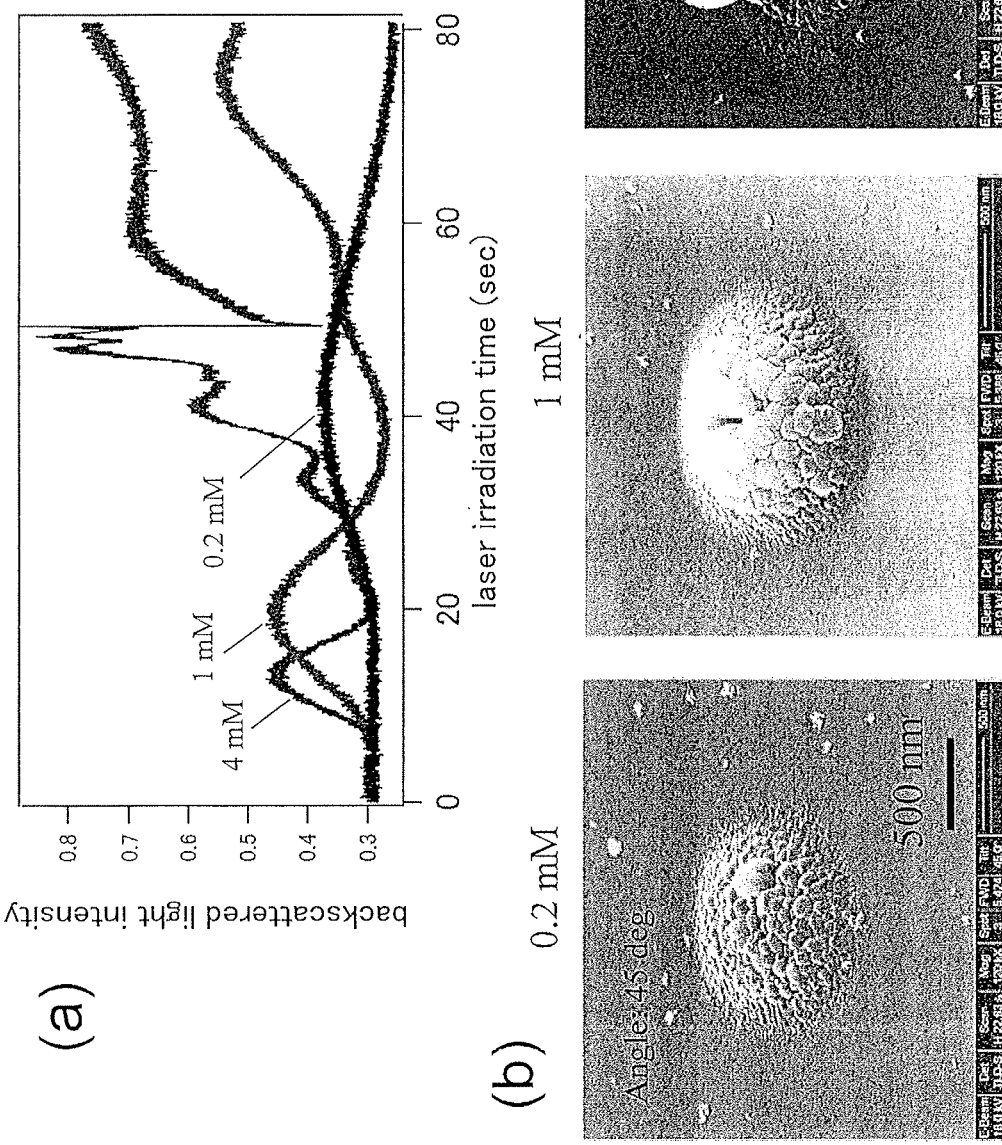

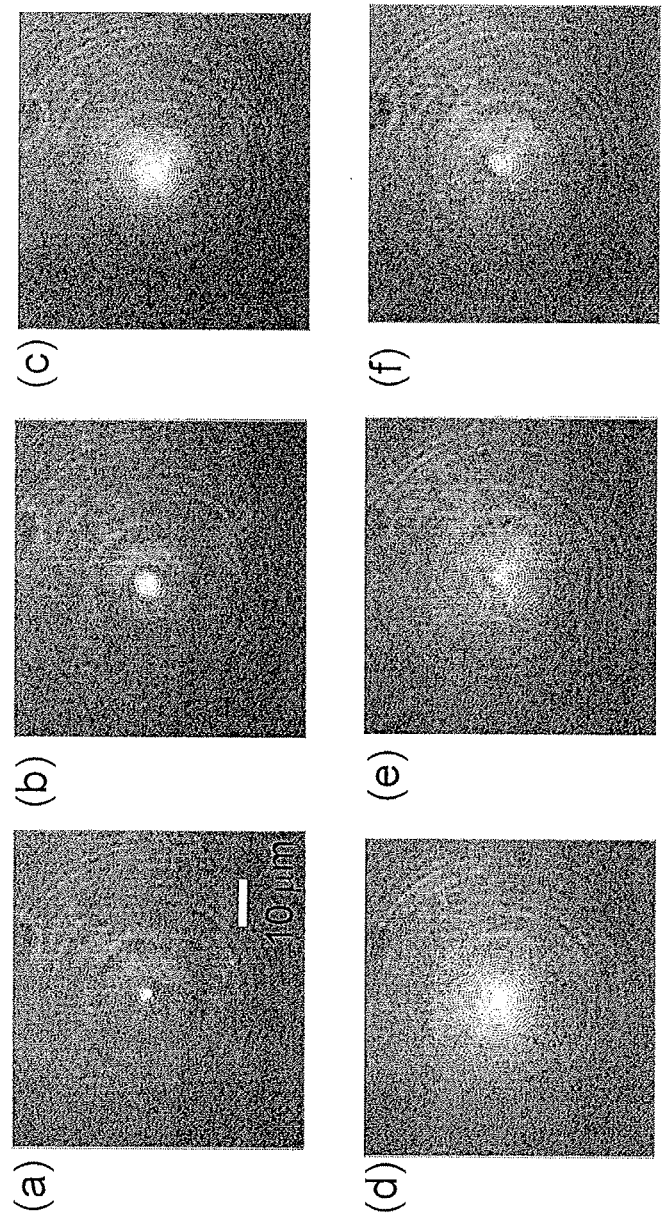
[FIG. 8]

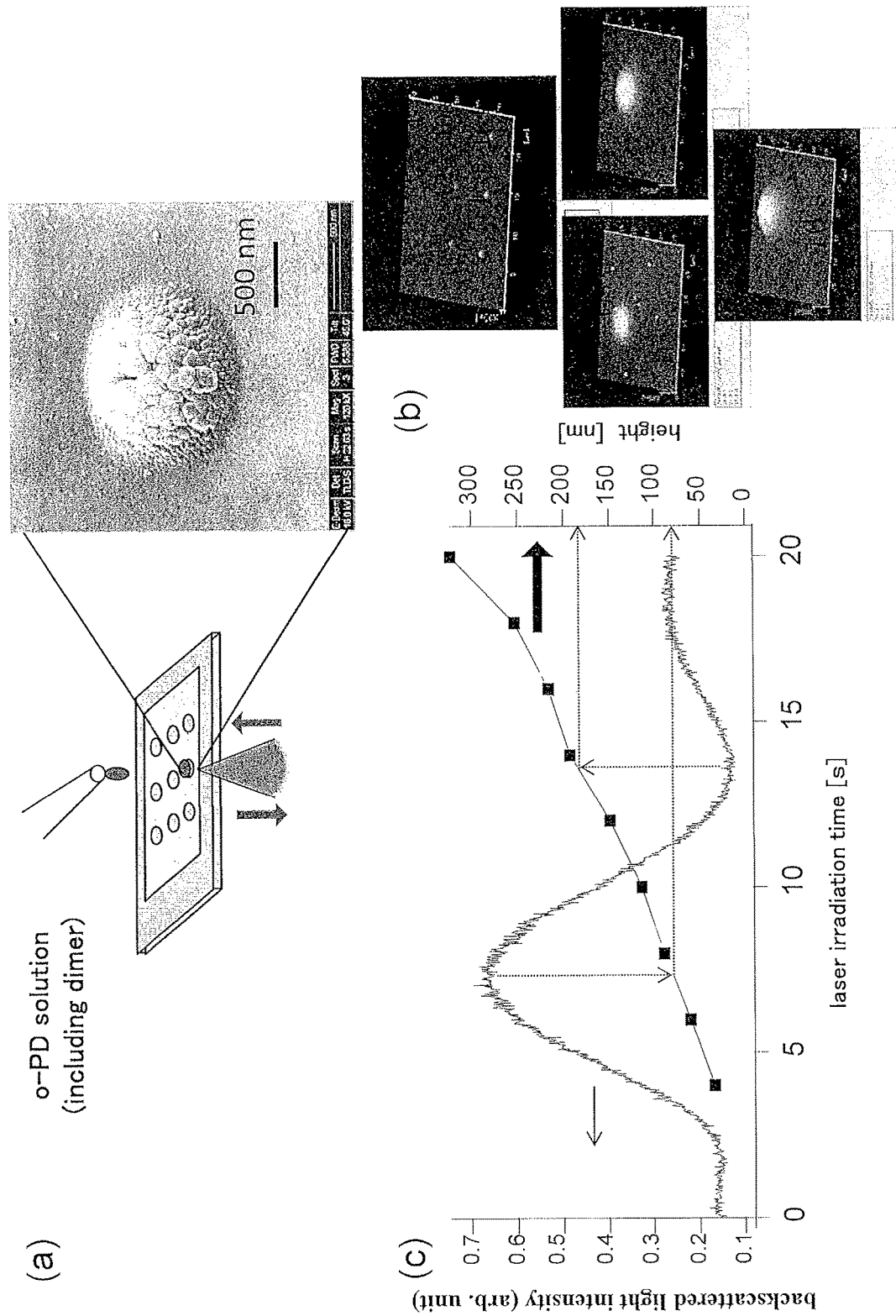
[FIG. 9]

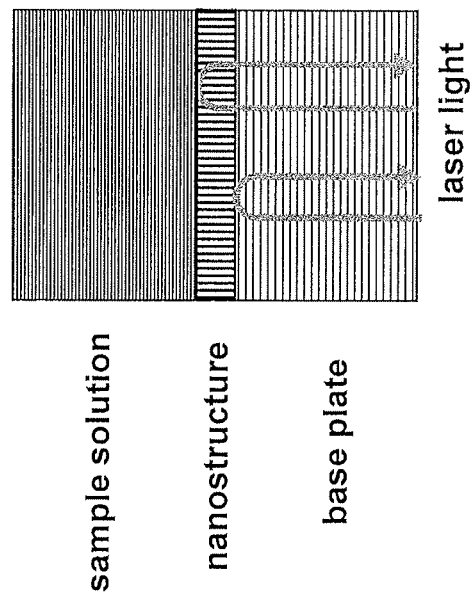
[FIG. 10]

[FIG. 11]
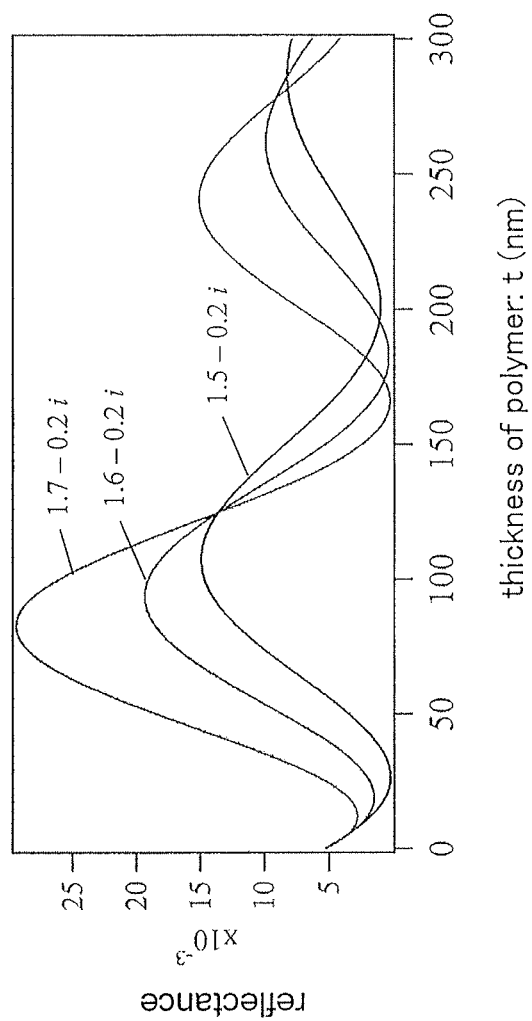

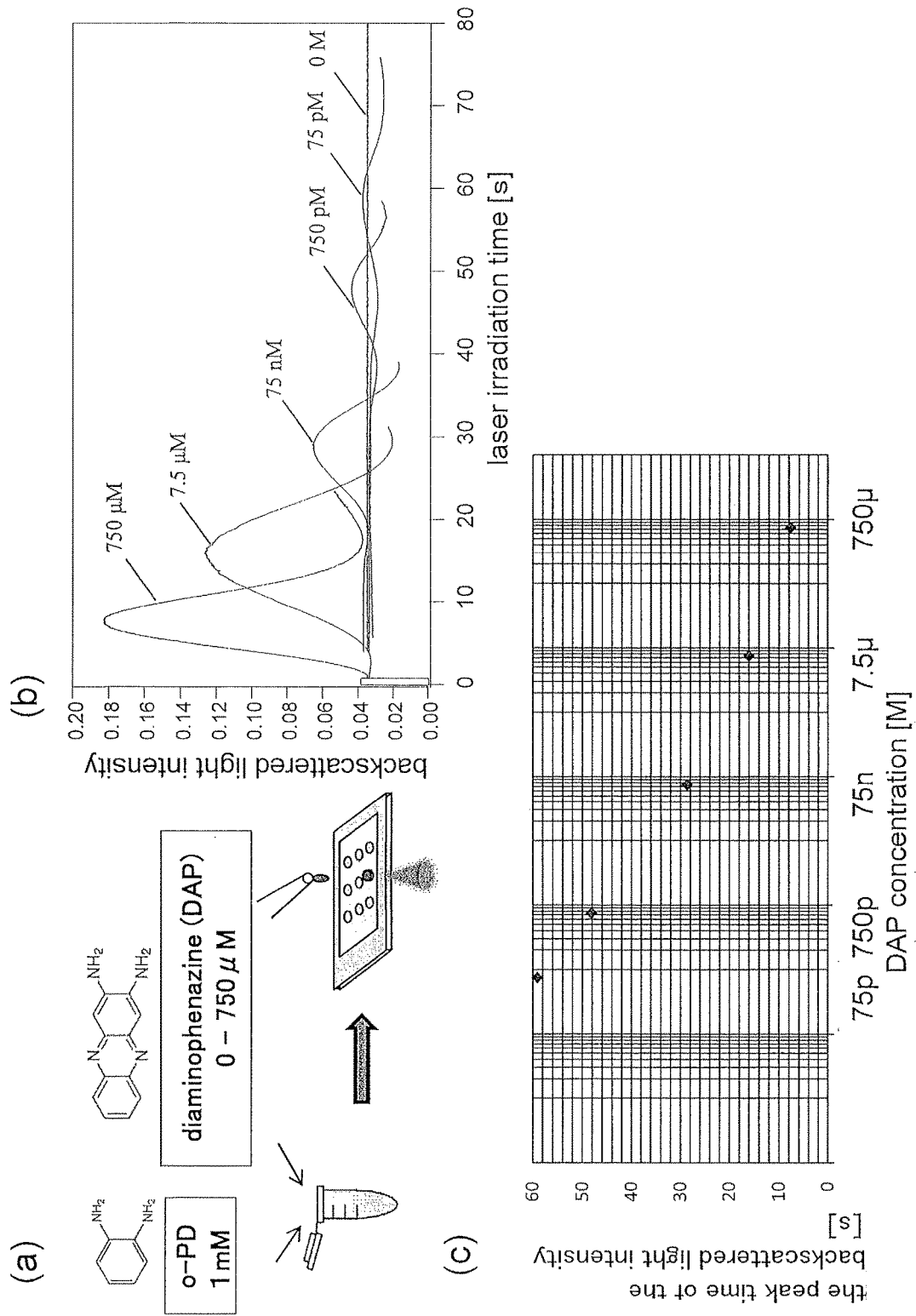
[FIG. 12]

[FIG. 13]
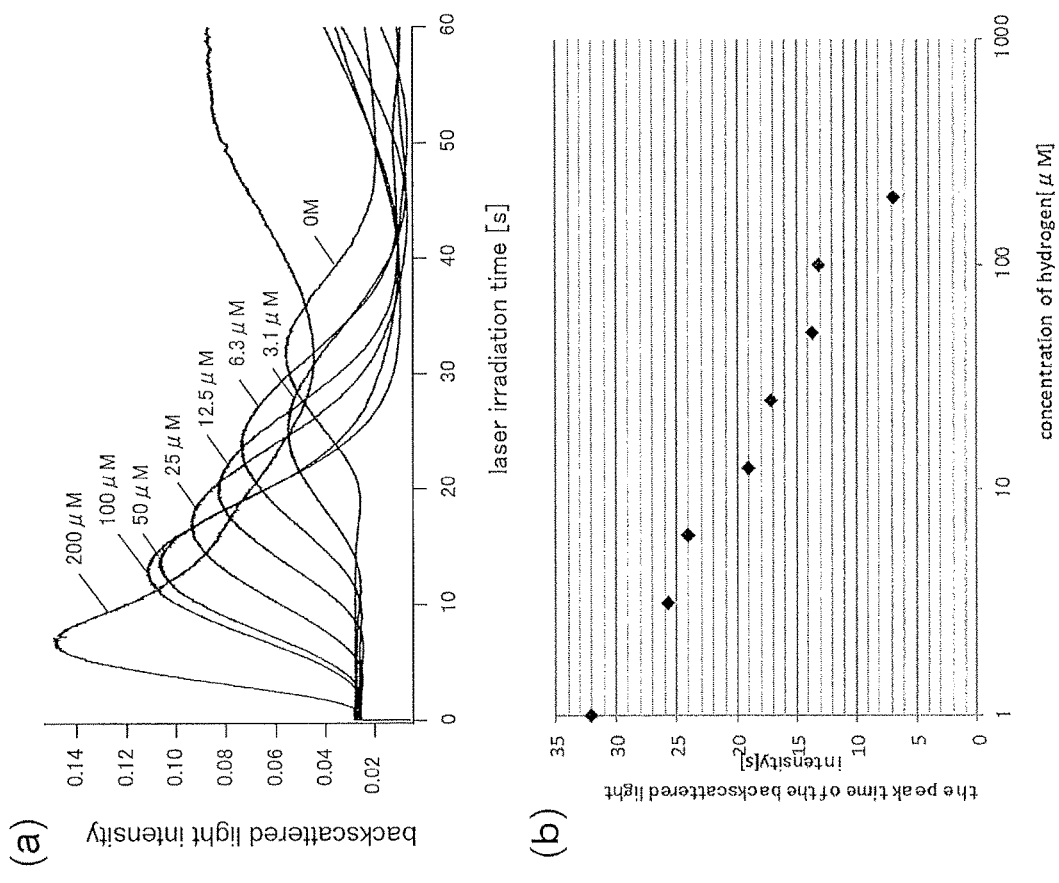

[FIG. 14]
(a) Structures formed at a focal point when a laser light was focused on o-PD solution
upper surface
diameter 1.5 μm   height 500 nm
45° degrees tilted
(b) Structures formed at a focal point when a laser light was focused on the mixture of the o-PD solution, the HRP solution and the hydrogen peroxide
upper surface
diameter 1.22 μm   height 1.15 μm
45° degrees tilted

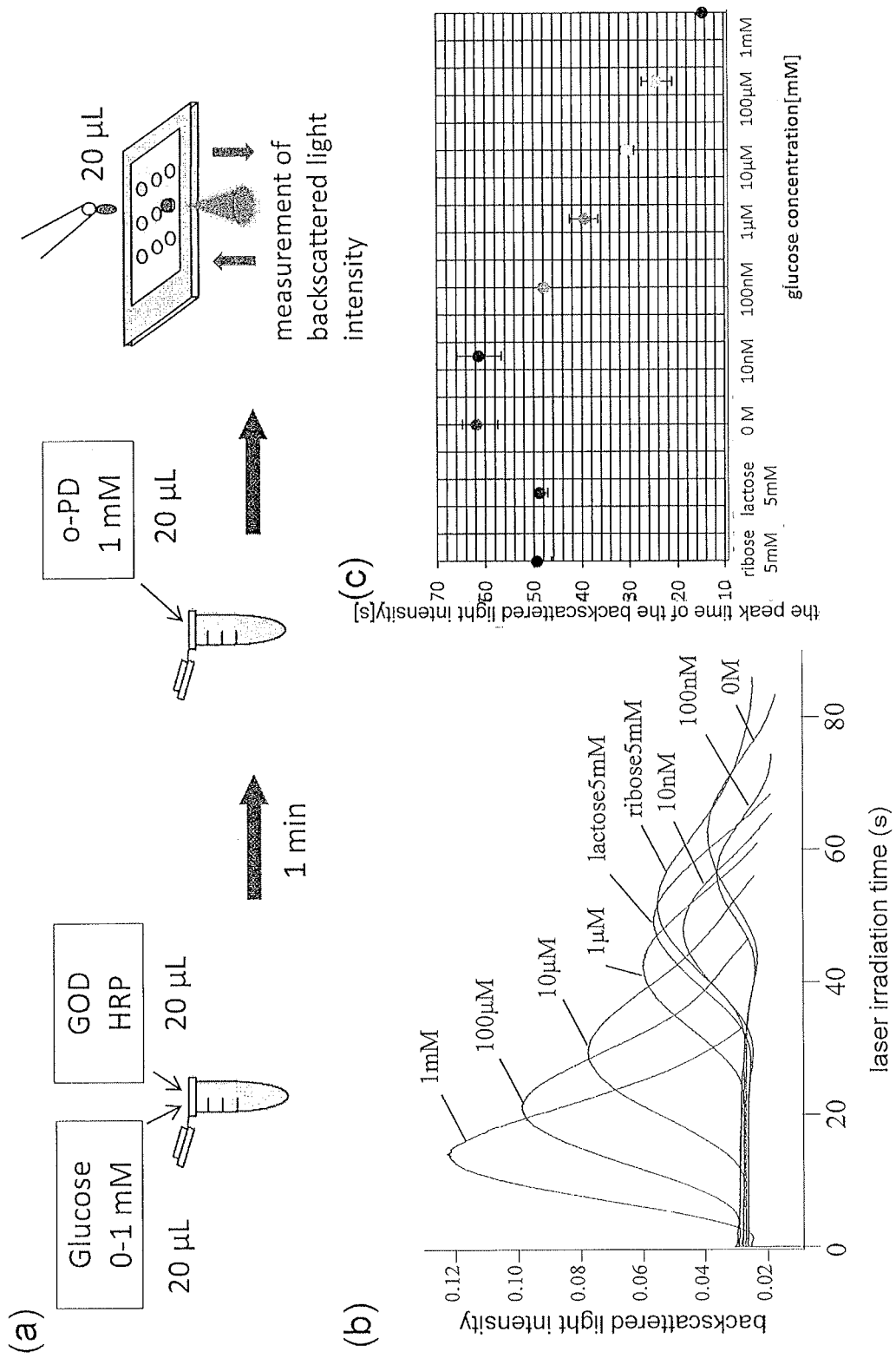
[FIG. 15]

[FIG. 16]
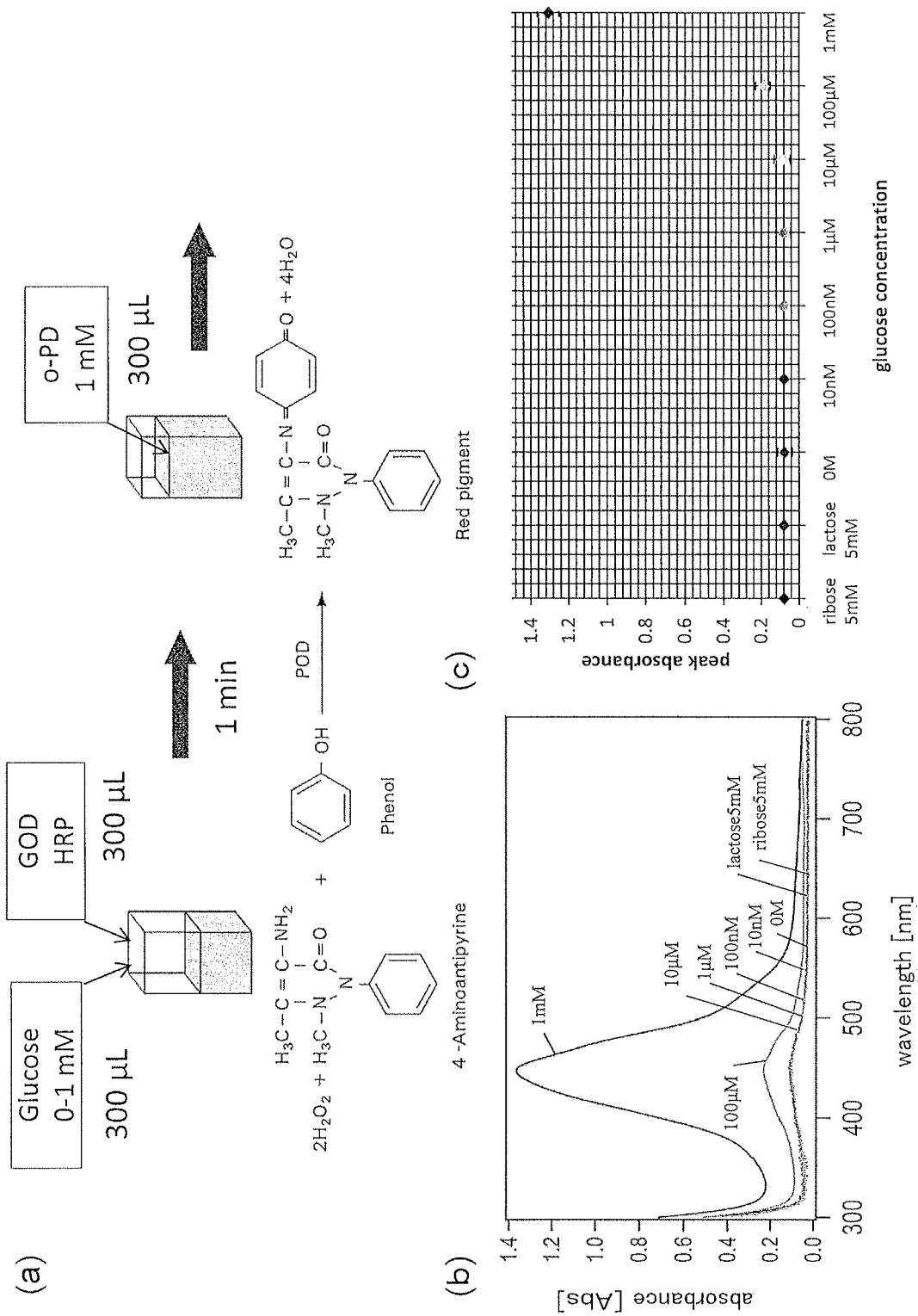

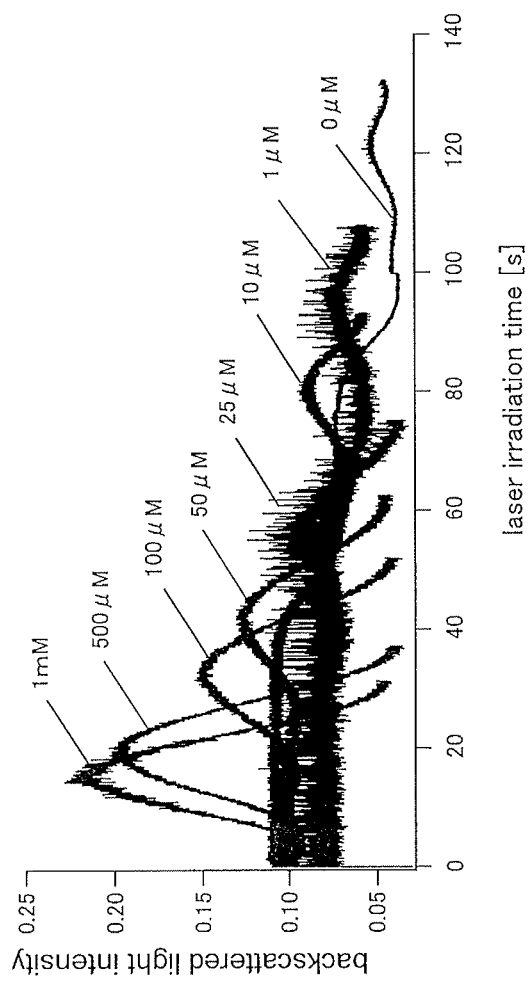
[FIG. 17]

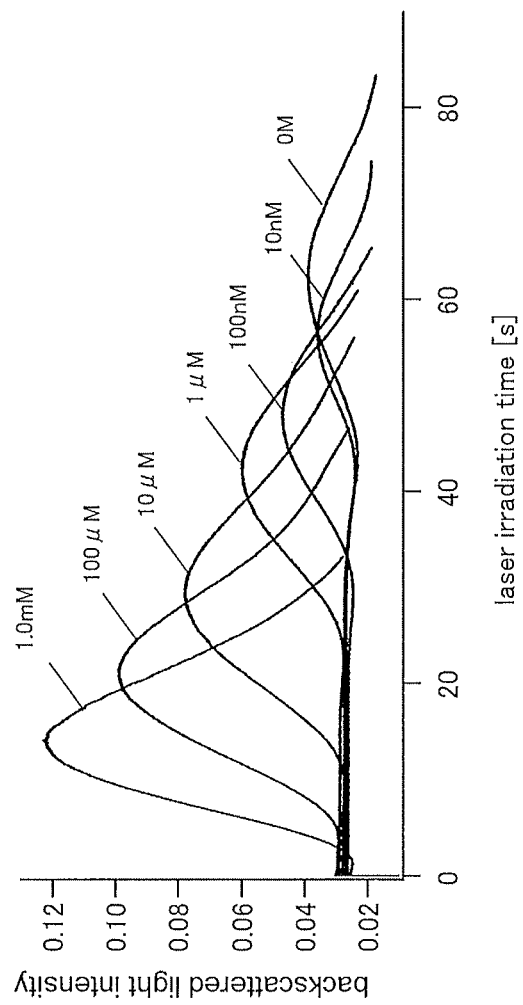
[FIG. 18]

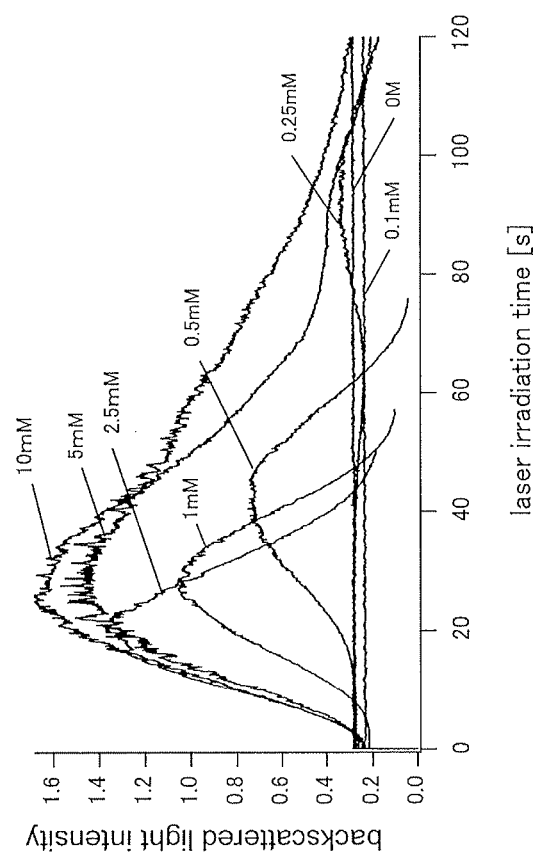
[FIG. 19]

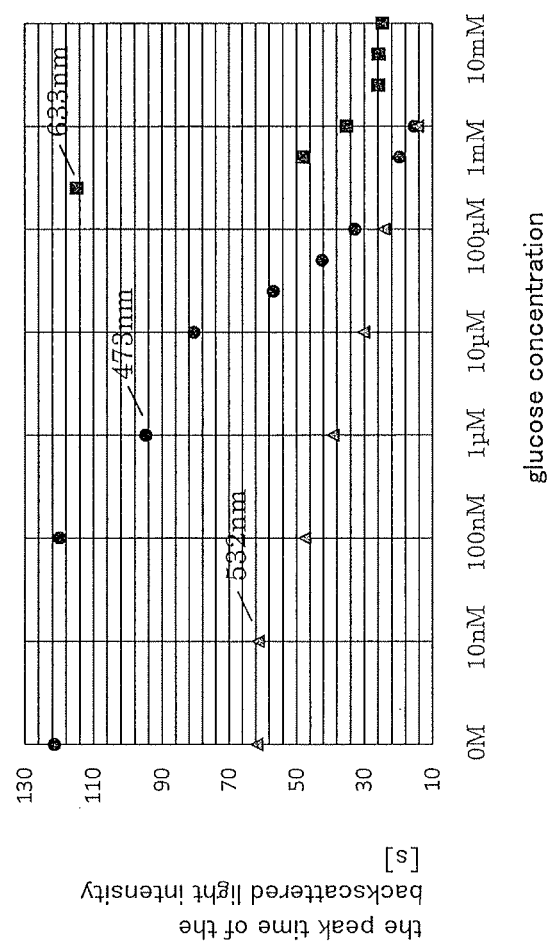
[FIG. 20]

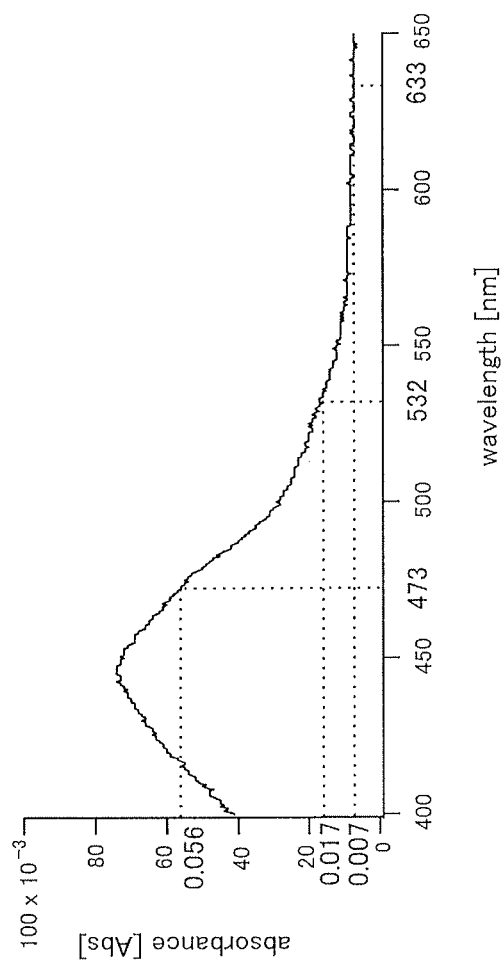
[FIG. 21]

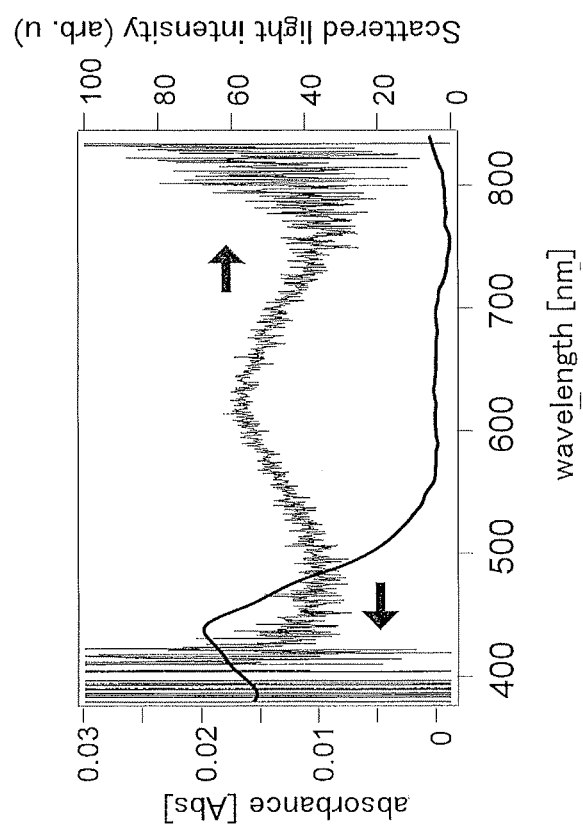
[FIG. 22]

[FIG. 23]
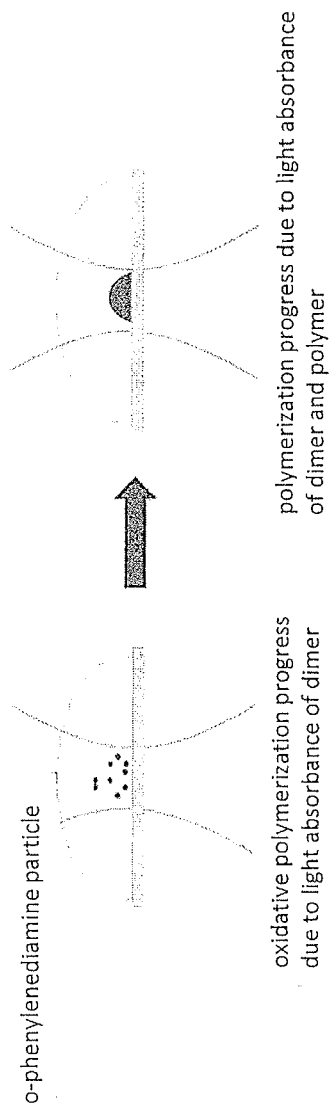

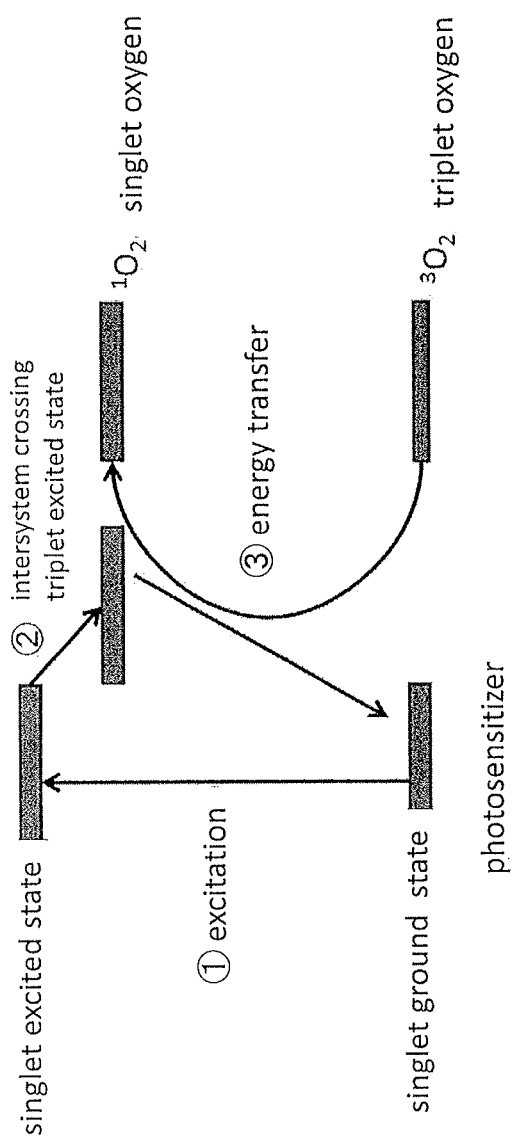
[FIG. 24]

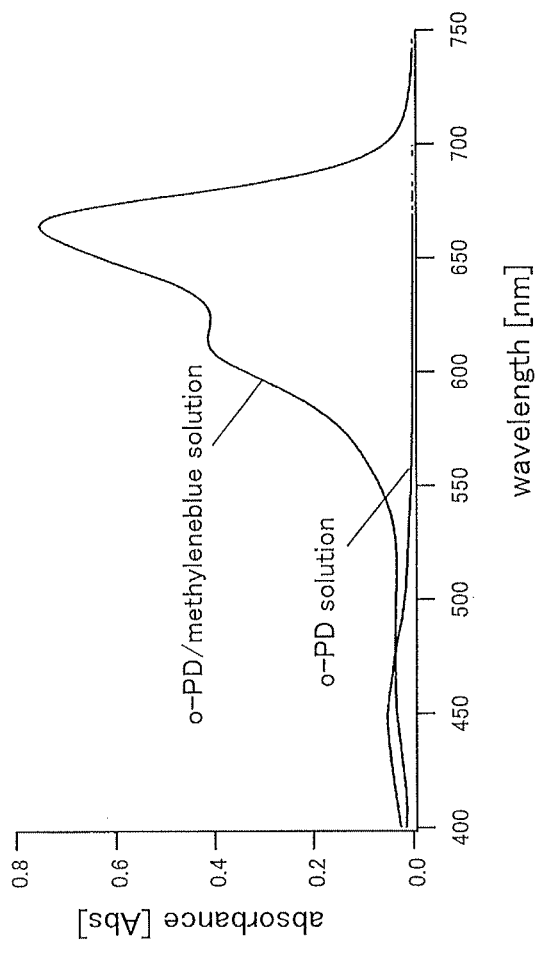
[FIG. 25]

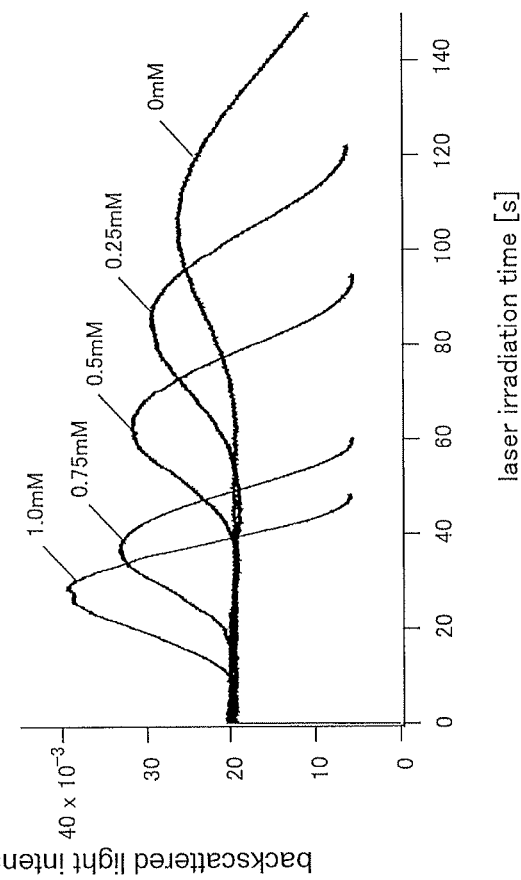
[FIG. 26]

[FIG. 27]
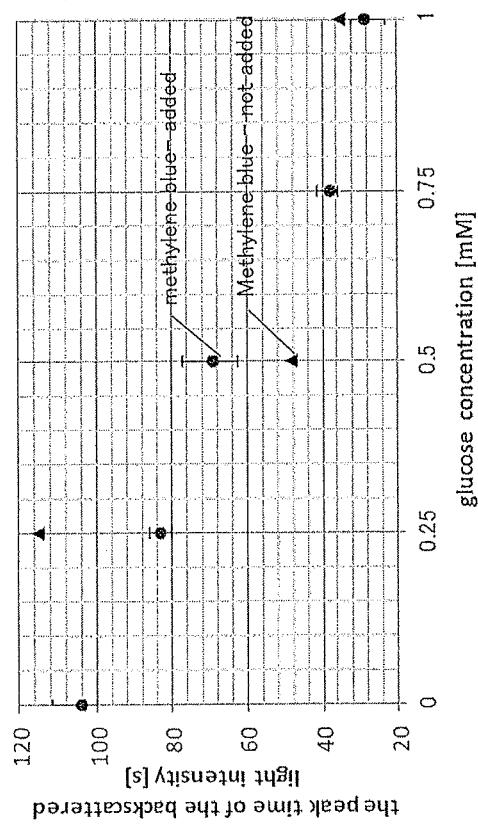

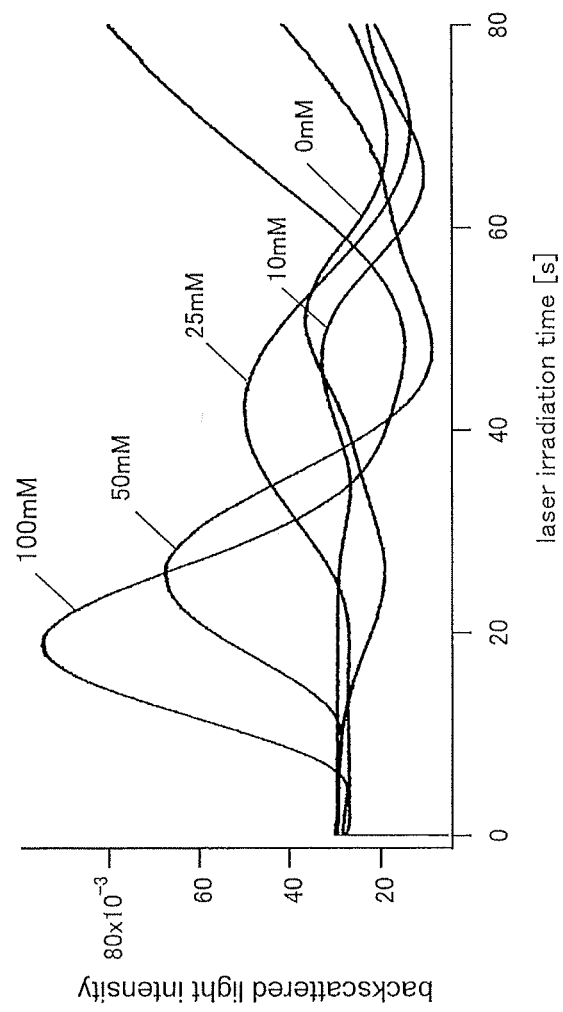
[FIG. 28]

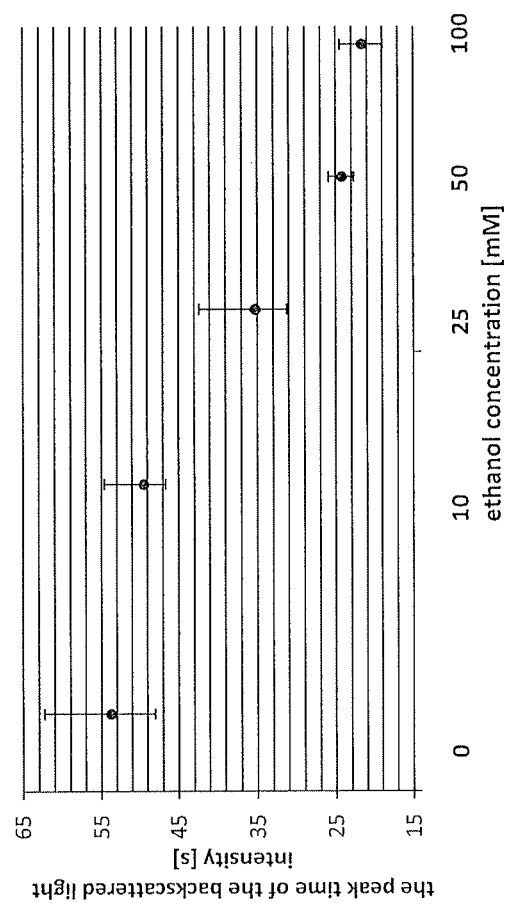
[FIG. 29]

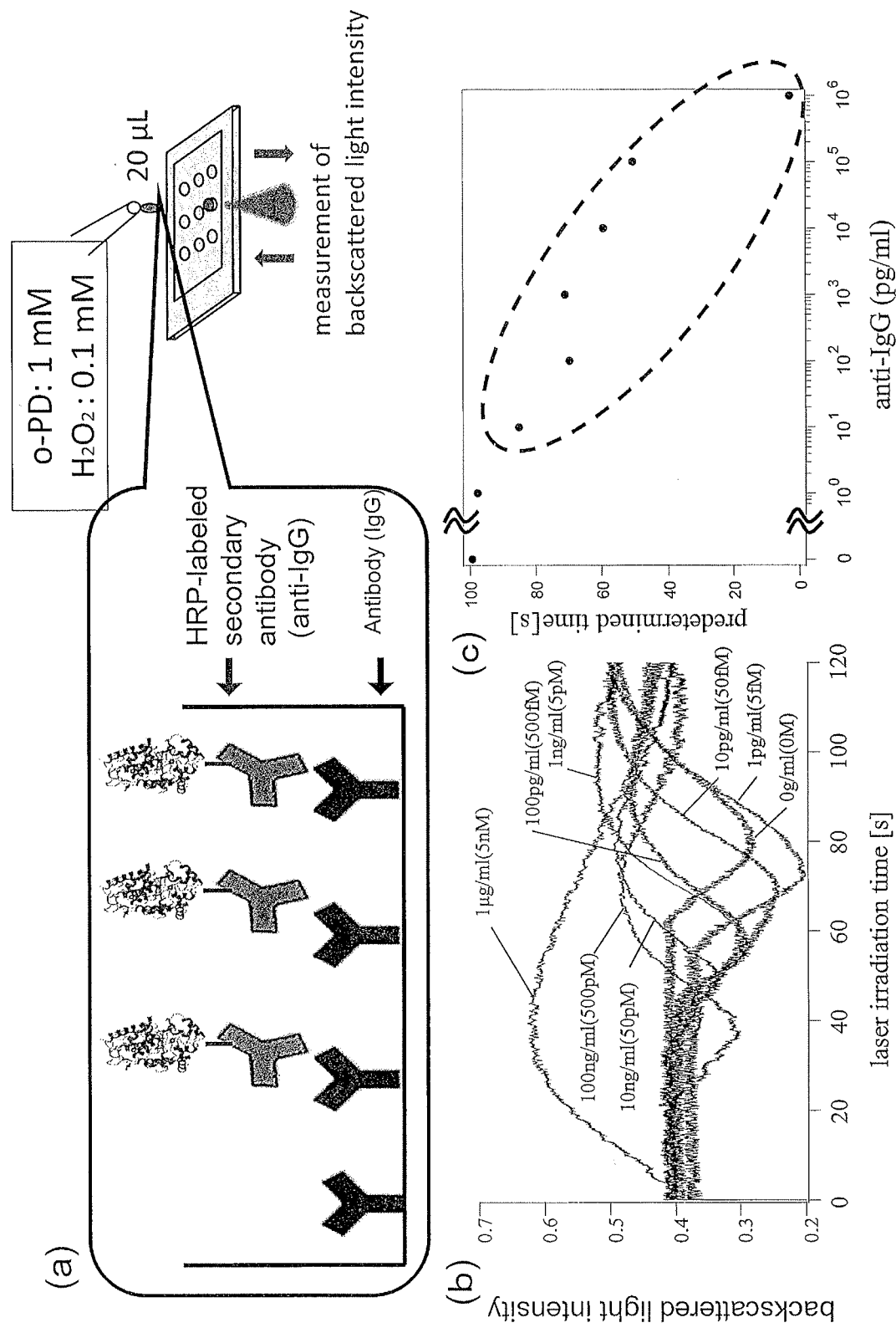

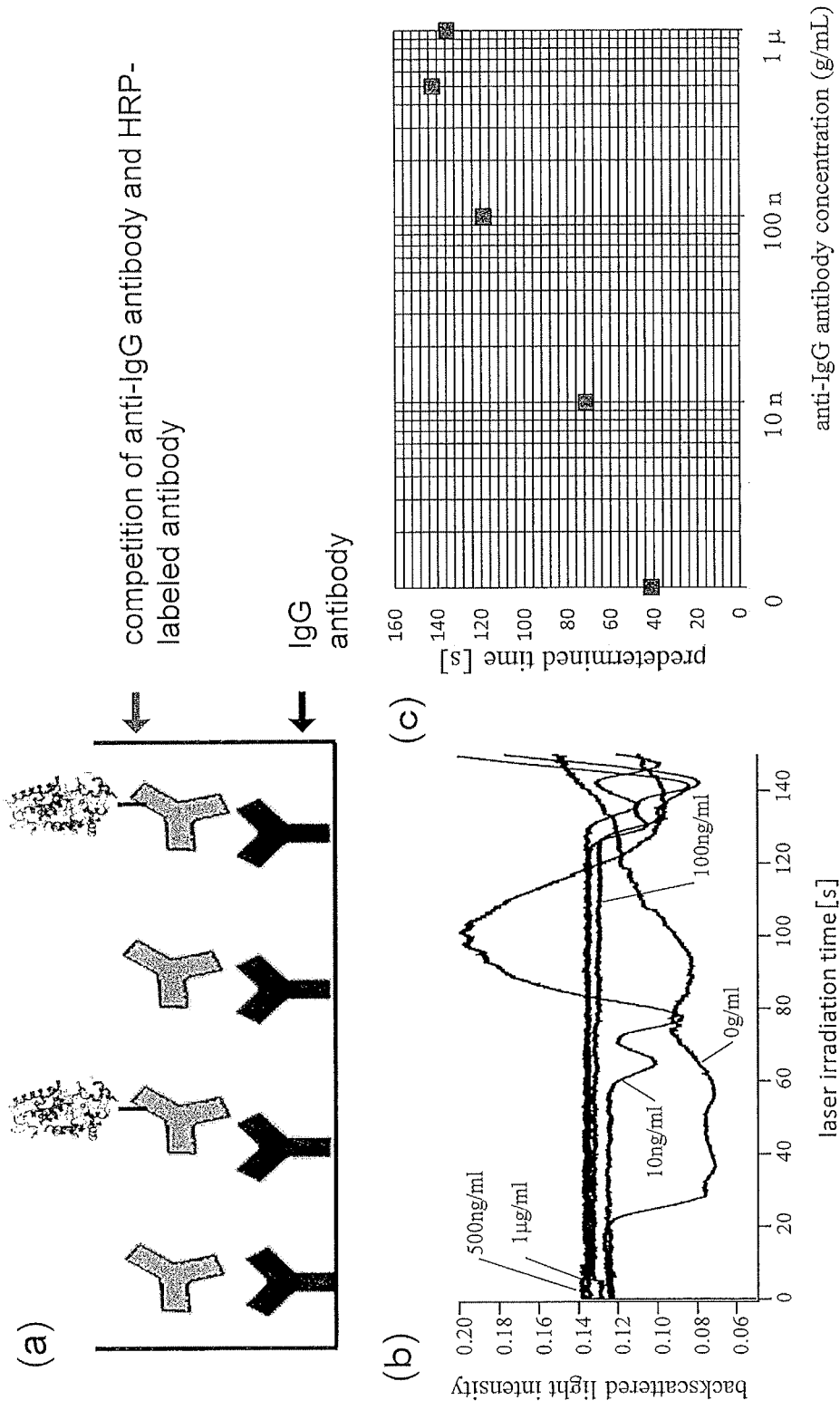
[FIG. 31]

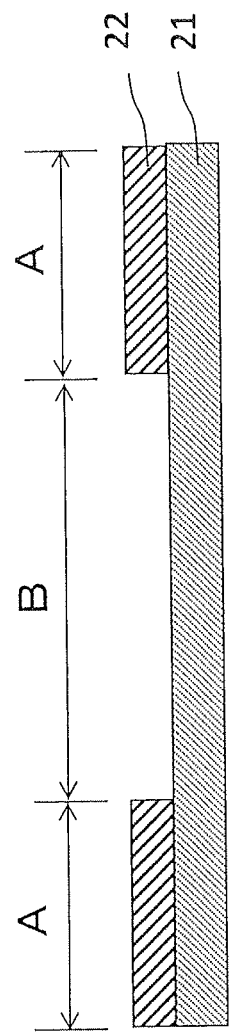
[FIG. 32]

[FIG. 33]
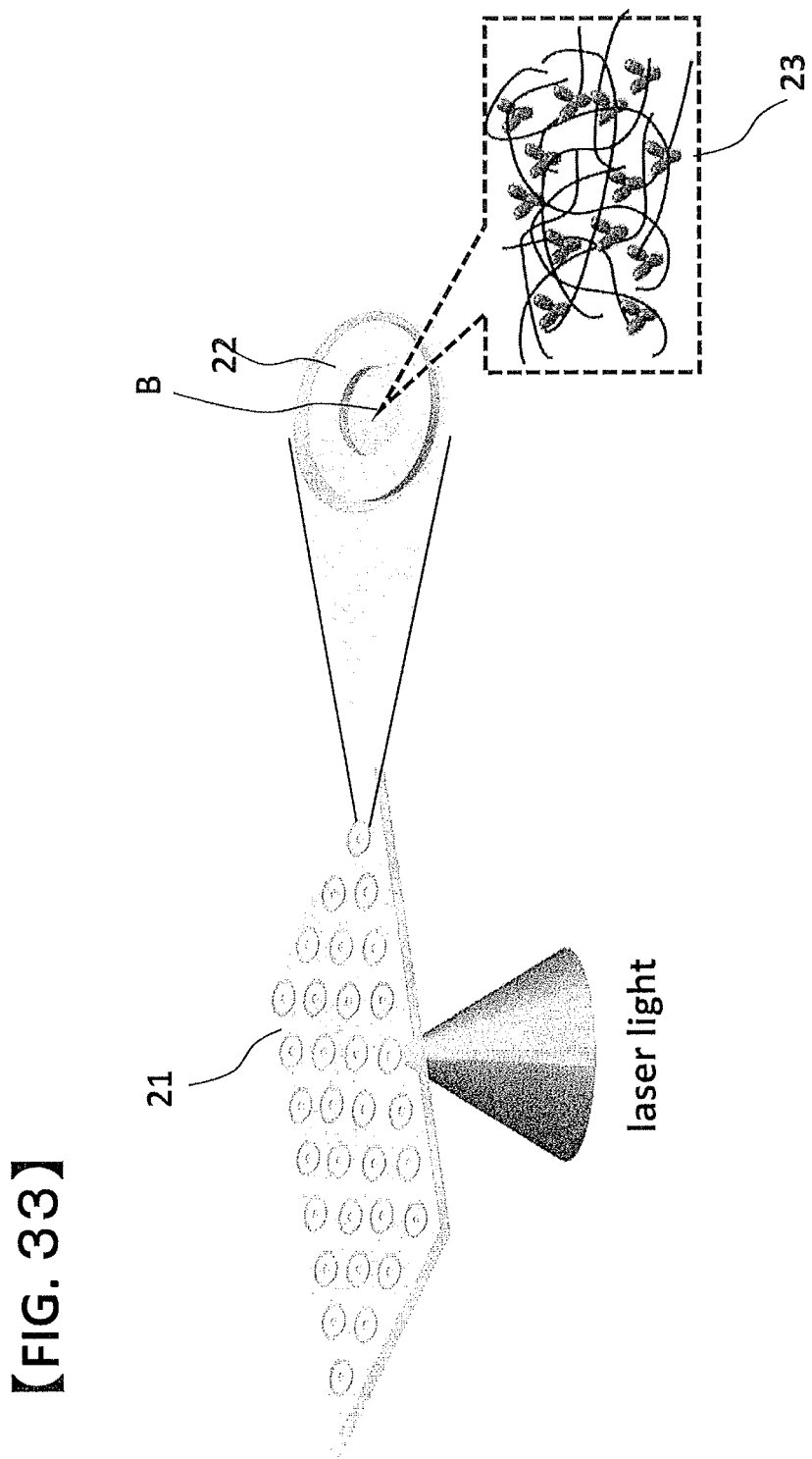

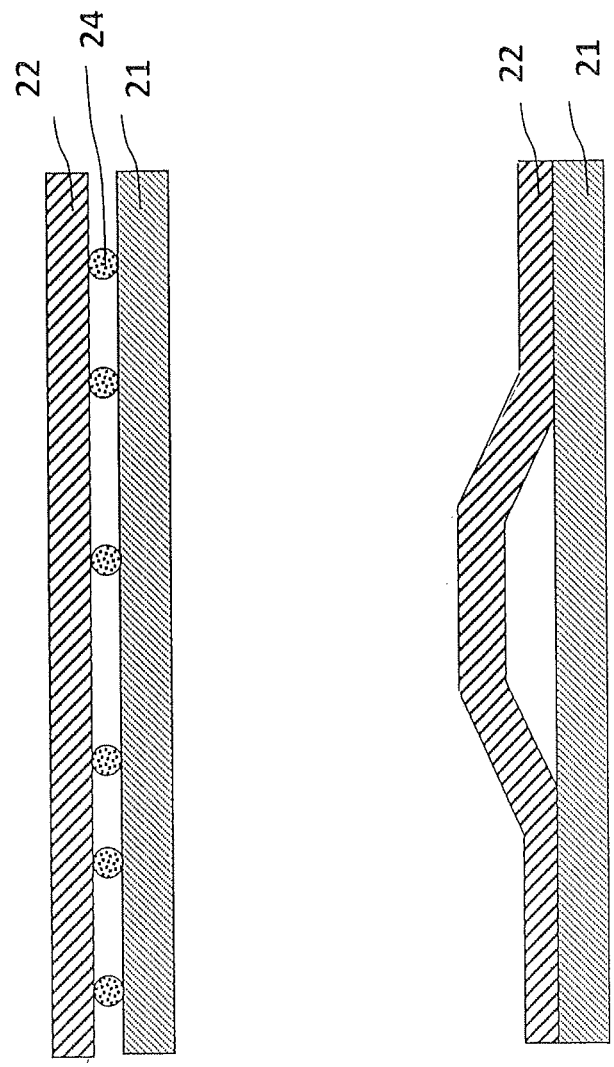

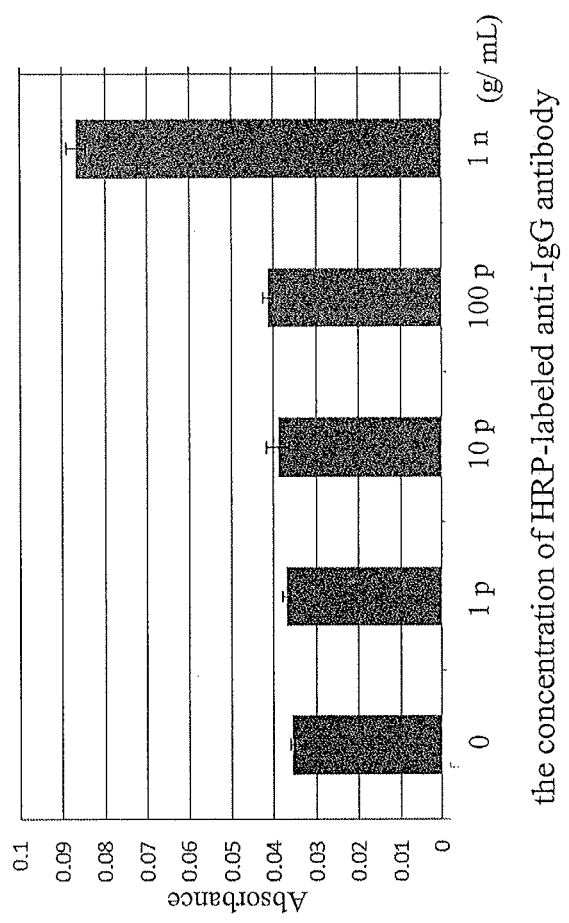
[FIG. 36]

[FIG. 37]
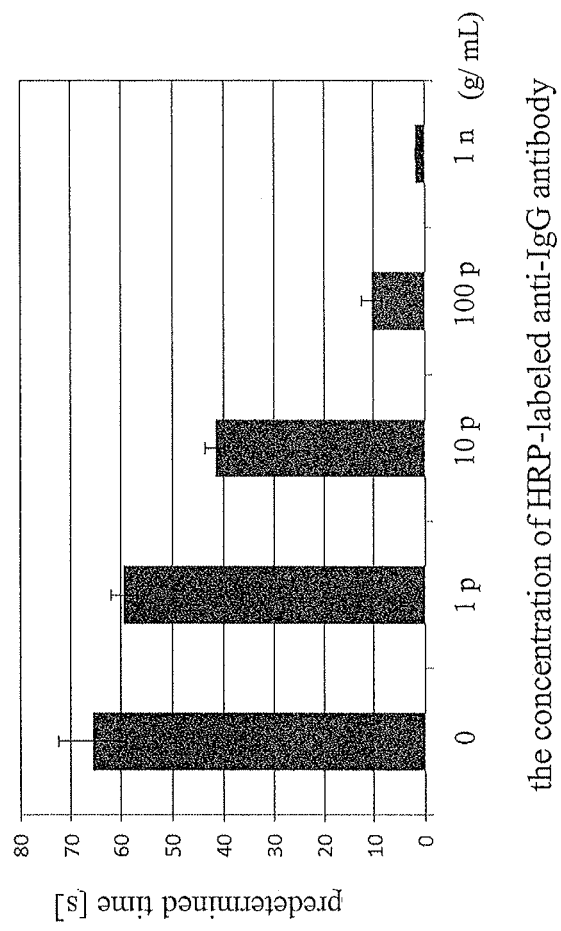
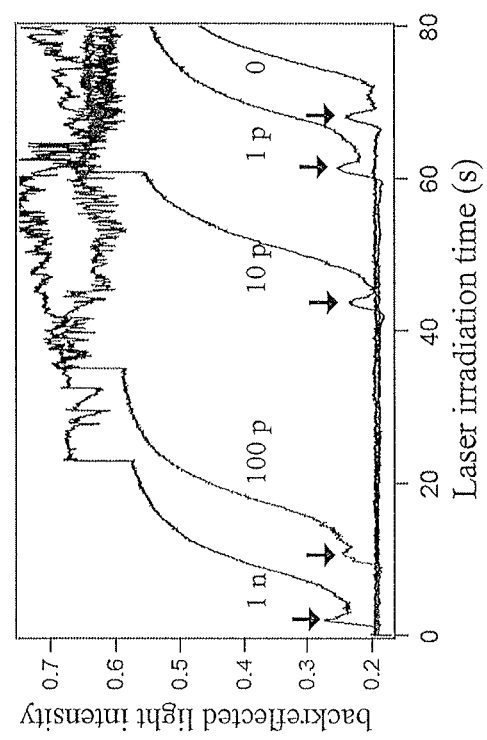

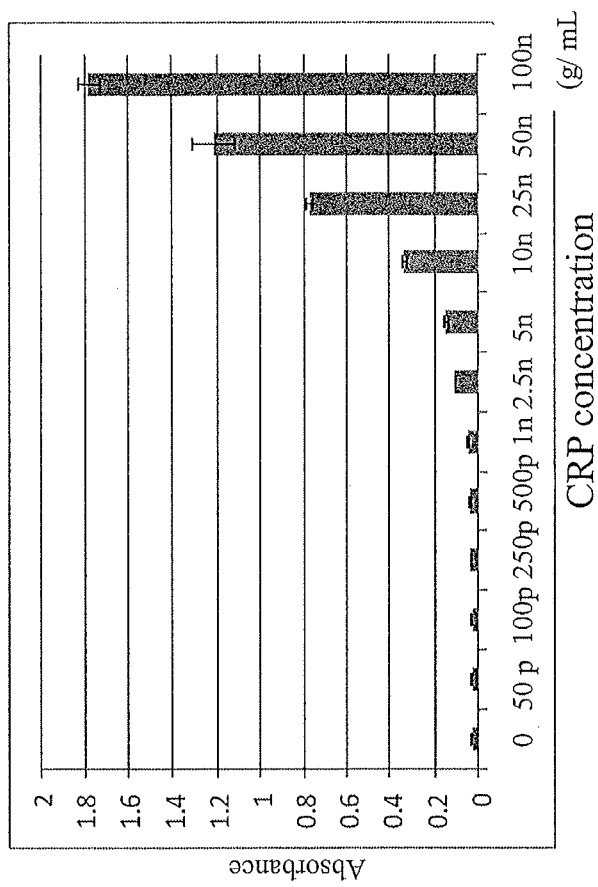
[FIG. 38]

[FIG. 39]
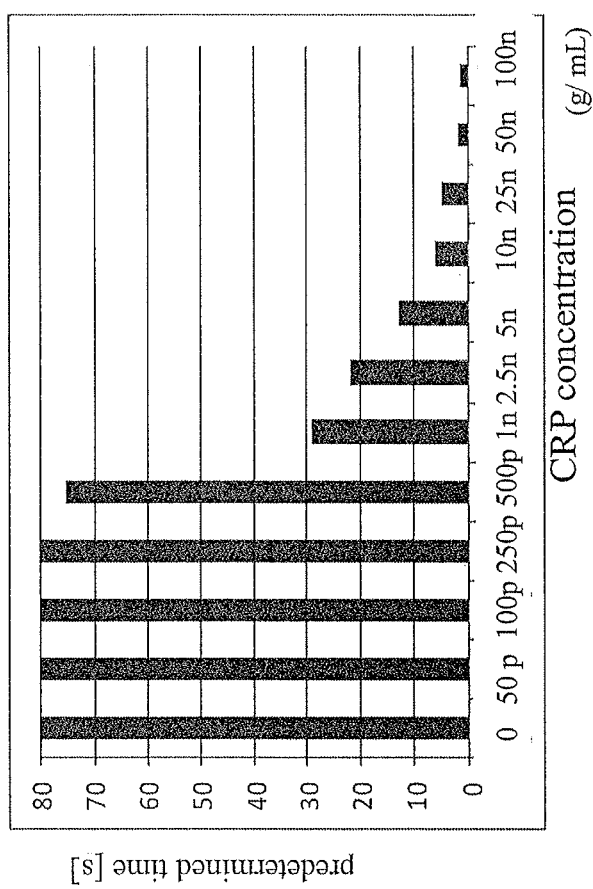
(a)
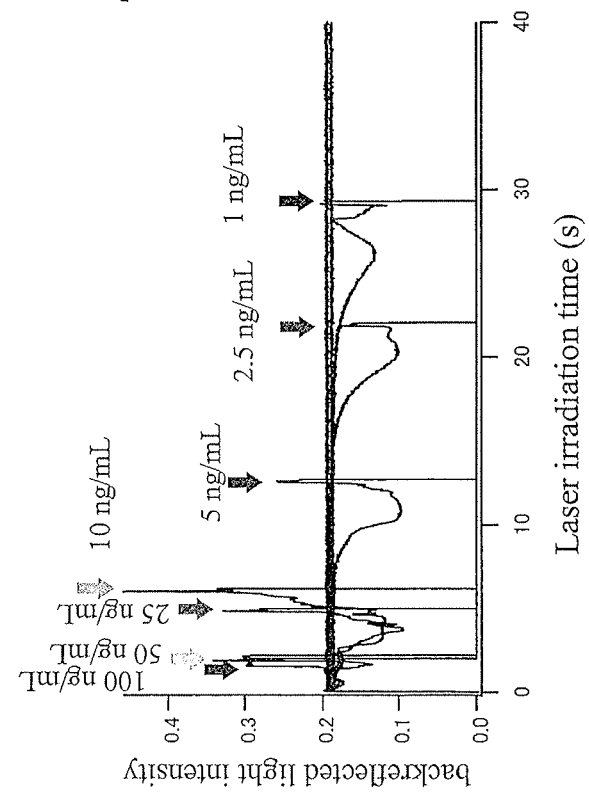
(b)

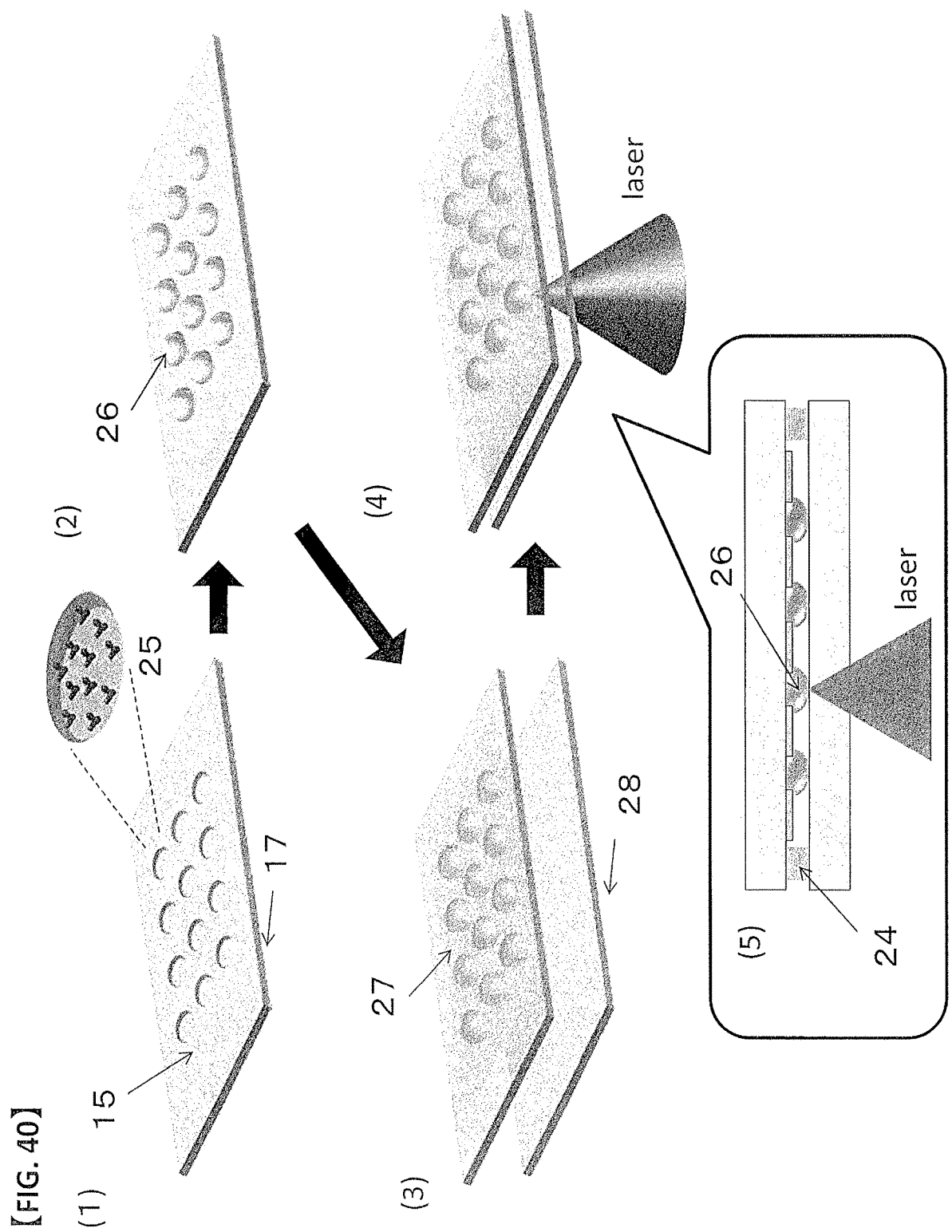

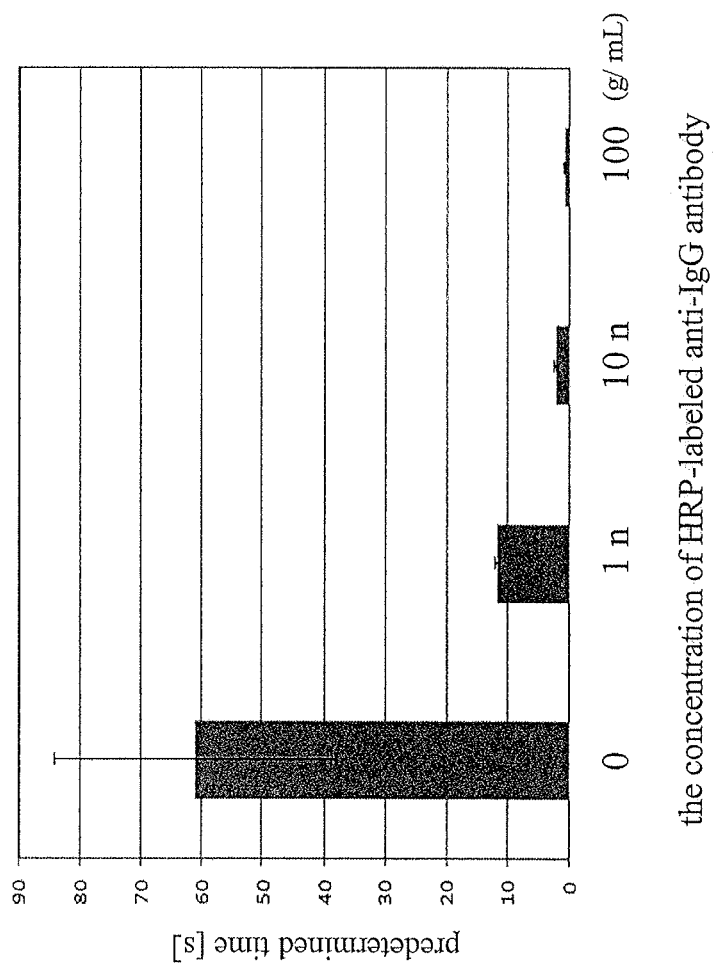
[FIG. 41]

METHOD FOR MEASURING CONCENTRATION OF TEST SUBSTANCE, AND DETECTION APPARATUS

TECHNICAL FIELD

The present invention relates to a method for detecting a test substance using an enzyme (oxidoreductase) such as peroxidase for producing a polymerized substance, and relates to a detection apparatus used for the method. Hereinafter, the present invention will be described using the ELISA method (Enzyme-Linked ImmunoSorbent Assay). However, the present invention is not limited thereto.

BACKGROUND ART

The ELISA method is a type of immunological measurement method (immunoassay) using a specific binding reaction between an epitope of an antigen and an antibody, and a color reaction by an enzyme labeled on an antibody or an antigen in combination. In the ELISA method, a highly specific antigen-antibody reaction is utilized and color development based on an enzyme reaction is converted into a signal, thereby enabling high sensitivity detection and superior quantitativity. Furthermore, the ELISA method has high safety and is inexpensive and simple as compared with radioimmunoassays (RIA) using radioactive substances as a labeling substance. Therefore, the ELISA method has been widely used for detection and quantification of various substances to be tested including biological substance such as antibodies, influenza viruses, plasma proteins, cytokines, DNA, peptides and ligands; chemicals such as pesticide residues and environmental hormones contained in food; diagnostic substances such as blood sugar and tumor markers used for diagnosis of diabetes, cancers, and the like.

The ELISA method is roughly classified into the direct adsorption method, the competitive method, and the sandwich method according to the difference of the measurement principles. Each of the measurement methods is summarized as follows.

In the direct adsorption method, a test substance is first immobilized on a microplate or the like, and then an antibody labeled with an enzyme (enzyme-labeled antibody) is added thereto and allowed to react with an antigen in the test substance (antigen-antibody reaction). Next, after removing impurities by washing, a chromogenic substrate against the labeling enzyme is added and allowed to react, and the absorbance of the dye developed is measured using a colorimeter to determine the amount of the antigen in the test substance. The direct adsorption method has disadvantages such as a low quantitativity of trace protein and the like.

The competitive method has been developed to improve the above disadvantages of the direct adsorption method, and is a method for detecting an antigen in a test substance with high sensitivity using one kind of antibody against the antigen. In the competitive method, a test substance and an enzyme-labeled antigen are first added to a microplate on which an antibody has been immobilized, and to be allowed to competitively react (antigen-antibody reaction). Next, after removing impurities by washing, a chromogenic substrate of the enzyme is added and allowed to react, and the absorbance of the dye developed is measured using a colorimeter to determine the amount of the antigen in the test substance.

The sandwich method is a method for detecting an antigen in a test substance using two kinds of antibodies and has an advantage of very high specificity. Specifically, a test substance is added to an antibody (primary antibody, capture antibody) immobilized on a microplate or the like and allowed to react (antigen-antibody reaction). After removing impurities by washing, an antibody (secondary antibody) labeled with an enzyme is further added and allowed to react at a different site from the site of the above antigen-antibody reaction. Accordingly, a sandwich structure of primary antibody-antigen-secondary antibody is formed. After removing impurities by washing, a chromogenic substrate of the enzyme is added and allowed to react, and the absorbance of the dye developed is measured using a colorimeter to determine the amount of the antigen in the test substance.

For example, when detecting antibodies such as IgG antibodies using the ELISA method, a color reaction using Horseradish peroxidase (HRP) and hydrogen peroxide ($H_2O_2$) which is a substrate of HRP as a labeling enzyme has been generally used. In addition to HRP, peroxidases such as glutathione peroxidase and haloperoxidase have been widely used for quantitative determination of, in addition to antibodies, biological components such as glucose and cholesterol. Peroxidases have a low substrate specificity to a substance to be oxidized, and various quantitative methods can be applied thereto. In particular, since the HRP described above has a small molecular weight, the HRP bound to the antibody is used as a labeling enzyme in the ELISA method, and the HRP which is combined with a chromogenic reagent (also referred to as a chromogenic substrate) has been utilized in the fields of medicine, epidemiology, clinical tests, and the like. For a color reaction using HRP, o-phenylenediamine (o-PD) that is a derivative of aniline is often used as a chromogenic substrate.

The reaction formula in which HRP and hydrogen peroxide ($H_2O_2$) are added to o-PD, and a polymerized substance of 2,3-diaminophenazine (DAP) is produced by an oxidative polymerization reaction is shown below.

[Chemical Formula 1]

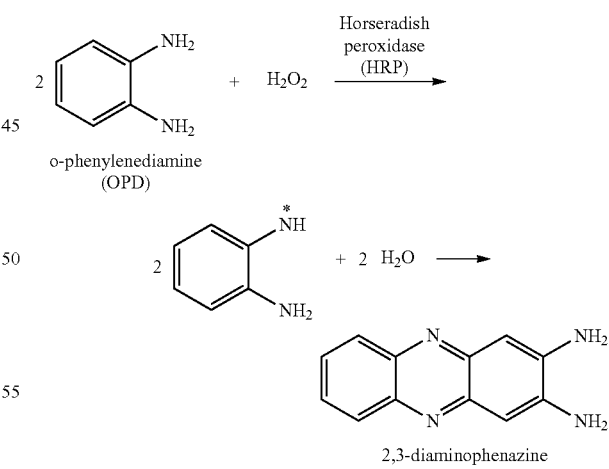

DAP obtained by the above reaction formula is an orange or red chromogenic substance, and the absorption peak at a wavelength of about 420 nm increases with time. By measuring the absorbance based on this color reaction, biological substances such as glucose and cholesterol as well as antibodies can also be detected.

A color reaction using β-D-glucose and enzyme glucose oxidase (GOD) that specifically acts only to β-D-glucose is shown below. When β-D-glucose is oxidized by GOD, D-glucono-o-lactone (gluconic acid) and hydrogen peroxide ($H_2O_2$) are produced. The produced hydrogen peroxide ($H_2O_2$) is supplied to a next reaction 2, and o-PD is oxidatively polymerized by HRP to produce DAP that is an orange dimer (polymerized substance).

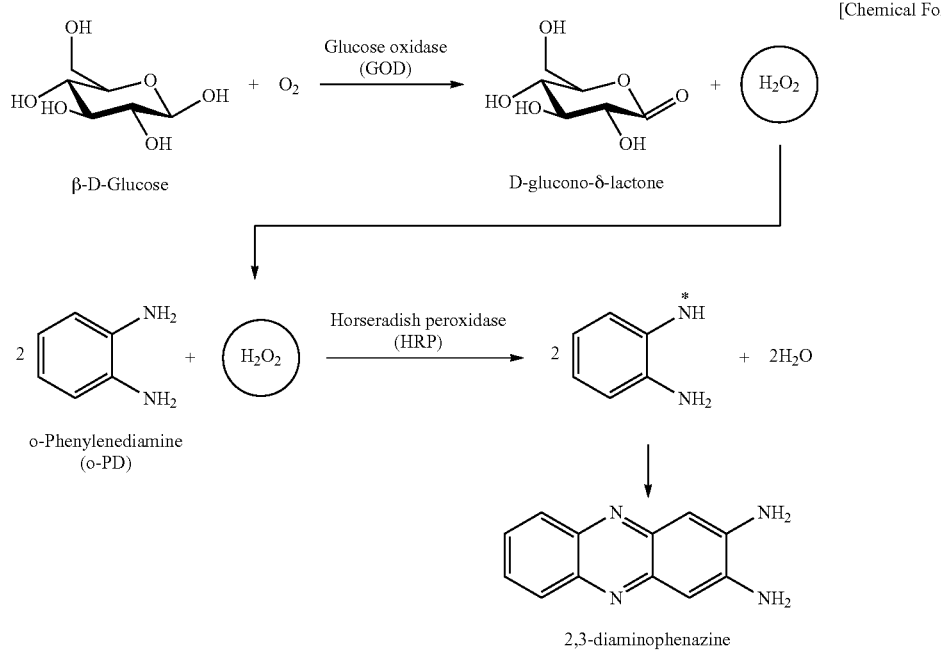

[Chemical Formula 2]

While the ELISA method includes several methods as described above, even in the case of using any of the above methods, the spectroscopic measurement of the dye developed by enzyme-labeled antibodies or the like is performed using a colorimeter. However, a plurality of devices such as a diffraction grating, optical filter, and high-sensitivity detector are required for the spectroscopic measurement, which leads to problems of an increase in size of an apparatus and an increase in cost.

Therefore, as a new detection technique applicable to the ELISA method and that can be replaced with conventional spectroscopic measurement methods, for example, a waveguide-based optical detection system with a scanning light source (Patent Document 1), a disk type analysis chip (Patent Document 2), an optical waveguide type antibody chip (Patent Document 3), and the like have been proposed.

PRIOR ART DOCUMENT

Patent Document

Patent Document 1: Japanese Patent Laid-open Publication (Kohyo) No. 2012-525595
Patent Document 2: Japanese Patent Laid-open Publication (Kokai) No. 2012-215515
Patent Document 3: Japanese Patent Laid-open Publication (Kokai) No. 2008-224524

DISCLOSURE OF THE INVENTION

Problems to be Solved by the Invention

As described above, the ELISA method using an antigen-antibody reaction and a labeling enzyme is extremely useful as means for sensitively and quantitatively detecting a trace amount of test substance. However, spectroscopic measurement devices used for measuring the absorbance of a chromogenic substance based on an enzyme reaction have a large size and also have a problem of a long measuring time.

The above problems are not limited to immunoassays such as the ELISA method and also founded in a method for detecting a test substance such as glucose by measuring the absorbance of a chromogenic substance generated by an enzyme reaction (such a method is included in enzyme assays in a broad sense because of the use of enzyme).

The present invention has been made in view of the above circumstances, and an object thereof is to provide a method for detecting a test substance utilizing a color development caused by an enzyme reaction, or a color development caused by a specific interaction such as an antigen-antibody reaction and an enzyme reaction, the test substance being detected rapidly, sensitively and quantitatively without using a spectroscopic measurement device.

Another object of the present invention is to provide a detection apparatus for detecting a test substance suitably used in the above method, the detection apparatus having a compact size and a short measuring time.

Means for Solving the Problems

One method for measuring a concentration of a test substance by the present invention which can solve the above problems comprises the steps of.
generating a peroxide from the test substance;
obtaining a polymerized substance by bringing an oxidoreductase for producing a polymerized substance and a substrate of the oxidoreductase for producing a polymerized substance into contact with the peroxide; and
irradiating the polymerized substance with light to record a temporal variation information of an intensity of scattered light generated from an irradiation point.

In a preferred embodiment of the present invention, the test substance comprises a substance that produces a peroxide by an enzyme reaction.

Another method for measuring a concentration of a test substance which can solve the above problems comprises the steps of:

obtaining a polymerized substance by bringing a modifier in which a substance having a specific interaction with the test substance is modified with an oxidoreductase for producing a polymerized substance into contact with the test substance, and then bringing a peroxide and a substrate of the oxidoreductase for producing a polymerized substance into contact with the test substance; and irradiating the polymerized substance with light to record a temporal variation information of an intensity of scattered light generated from an irradiation point.

In a preferred embodiment of the present invention, the specific interaction with the test substance is an antigen-antibody reaction.

In a preferred embodiment of the present invention, the temporal variation information constitutes a signal waveform, the method further comprises the step of identifying a time taken from a predetermined time point on and after a start of irradiation of the light to the test substance until the signal waveform shows an extremum.

In a preferred embodiment of the present invention, the obtaining step of a polymerized substance is performed on a base.

In a preferred embodiment of the present invention, a first base on which at least one of group X substances consisting of the test substance and the substance having a specific interaction with the test substance exists, and a second base on which at least one of group X substances consisting of the test substance and the substance having a specific interaction with the test substance does not exist are stacked, and irradiation of light is performed from the second base side.

In a preferred embodiment of the present invention, the base comprises a group X substance existing region where at least one of group X substances consisting of the test substance and the substance having a specific interaction with the test substance exists, and a group X substance non-existing region where the group X substance does not exist, and the group X substance non-existing region is irradiated with the light.

In a preferred embodiment of the present invention, a porous support is provided on the base, and the group X substance is immobilized with the porous support.

The detection apparatus for detecting a test substance of the present invention which can solve the above problems comprises:

a light source allowing light to enter the test substance;

a photoelectric conversion element detecting scattered light generated from a polymerized substance derived from the test substance; and a recording medium continuously recording a signal output from the photoelectric conversion element during a predetermined period of time.

In a preferred embodiment of the present invention, the polymerized substance derived from the test substance exists on a first surface side of a light-transmitting base, and wherein the detection apparatus further comprises a lens facing a second surface side of the light transmitting base.

In a preferred embodiment of the present invention, the detection apparatus further comprises the a calculating means identifying a time taken from a predetermined time point on and after a start of irradiation of the light to the polymerized substance derived from the test substance until a signal waveform recorded in the recording medium shows an extremum.

In a preferred embodiment of the present invention, the detection apparatus comprises on the first surface side of the light transmitting base, a group X substance existing region where at least one of group X substances consisting of the polymerized substance derived from the test substance and a substance having a specific interaction with the polymerized substance derived from the test substance exists, and a group X substance non-existing region where the group X substance does not exist.

Effects of the Invention

According to the present invention, the concentration of a test substance can be rapidly, quantitatively and sensitively measured and detected compared with conventional methods utilizing a spectrometer.

Furthermore, according to the present invention, it is possible to provide a small-sized and inexpensive detection apparatus having a short measurement time compared with conventional detection apparatuses utilizing a spectrometer.

BRIEF DESCRIPTION OF THE DRAWINGS

FIG. 1 is a diagram in which a method of the present invention and a conventional method are compared as to a method for detecting β-D-Glucose.

FIG. 2 is a diagram showing a reaction mechanism inferred in the present invention.

FIG. 3 is a diagram showing one embodiment of a detection apparatus used in the present invention.

FIG. 4 is a diagram illustrating a base plate using in the experiment.

FIG. 5 (a) shows the results of the absorption spectrum of the o-PD solution in each irradiation time when irradiating the o-PD solution with a green LED, and FIG. 5 (b) shows the temporal variations of the backscattered light intensities when a laser light is focused on each of the o-PD solutions differing in irradiation time to measure backscattered light intensities.

FIG. 6 is a diagram in which the peak time of the backscattered light intensity with respect to the peak absorbance value of the o-PD solution is plotted.

FIG. 7 (a) shows the relationship between the laser irradiation time and the backscattered light intensity when a green laser light was focused on the o-PD solutions having different concentrations, and FIG. 7 (b) shows SEM photographs after irradiating the o-PD solution having each concentration with a green laser for 80 seconds.

FIG. 8 (a) to 8 (f) are photographs of the images of reflected light taken every 4 seconds when a green laser was focused on an o-PD solution of 1 mM.

FIG. 9 (a) is a diagram illustrating a measurement procedure of the present experiment, FIG. 9 (b) shows AFM observation images when irradiated with laser for 4 seconds to 16 seconds, and FIG. 9 (c) shows the relationship between the laser irradiation time and the backscattered light intensity, and the relationship between the laser irradiation time and the height of a polymer.

FIG. 10 schematically shows the lights detected in the present invention.

FIG. 11 (a) illustrates a model sample sandwiched between a glass plate and water used in the experiment, and FIG. 11 (b) shows the relationship between the thickness and the reflectance of a polymer thin film in the model sample.

FIG. 12 (a) illustrates a measurement procedure of the present experiment, FIG. 12 (b) shows the temporal variations in the backscattered light intensities when a laser light is focused on a solution prepared by mixing an o-PD solution of 1 mM and each of DAPs having different concentrations, and FIG. 12 (c) shows the relationship between the concentration of DAP and the peak time of the backscattered light intensity.

FIG. 13 (a) shows the relationship between the laser irradiation time and the backscattered light intensity for a mixed solution of a HRP solution, each of hydrogen peroxides having different concentrations, and an o-PD solution, and FIG. 13 (b) shows the relationship between the concentration of hydrogen peroxide and the peak time of the backscattered light intensity.

FIG. 14 (a) shows SEM observation images when a laser light was focused on the o-PD solution, and FIG. 14 (b) shows SEM observation images of nanostructures formed at a focal point when a laser light was focused on the mixture of the o-PD solution, the HRP solution and the hydrogen peroxide.

FIG. 15 (a) illustrates a measurement procedure of the present experiment, FIG. 15 (b) shows the relationship between the laser irradiation time and the backscattered light intensity when a mixed solution of each of glucose aqueous solutions having different concentrations, GOD, and HRP was irradiated with laser, and FIG. 15 (c) is a diagram in which a time when the first peak of the backscattered light intensity appeared with respect to each glucose concentration is plotted.

FIG. 16 (a) illustrates a measurement procedure of the present experiment, FIG. 16 (b) shows the results of absorption spectrum of a mixed solution of each of glucose aqueous solutions having different concentrations, GOD, and HRP, and FIG. 16 (c) is a diagram in which the peak absorbance with respect to each glucose concentration is plotted.

FIG. 17 shows the temporal variations in the backscattered light intensities when glucoses having different concentrations were irradiated with a laser having a wavelength of 473 nm.

FIG. 18 shows the temporal variations of the backscattered light intensity when glucoses having different concentrations were irradiated with a laser having a wavelength of 532 nm.

FIG. 19 shows the temporal variations of the backscattered light intensity when glucoses having different concentrations were irradiated with a laser having a wavelength of 633 nm.

FIG. 20 shows the peak time of the backscattered light intensity with respect to the glucose concentration at each wavelength.

FIG. 21 shows the absorption spectrum of an o-PD solution (3.8 mM) used in the experiment.

FIG. 22 shows the relationship between the absorption spectrum of the o-PD aqueous solution (left axis) and the backscattered light intensity spectrum of a nanostructure formed by focusing laser on the o-PD aqueous solution (right axis) at each wavelength.

FIG. 23 is a schematic diagram showing the progress of an oxidative polymerization reaction of o-PD by a focused laser light.

FIG. 24 is a diagram illustrating the energy diagram of a photosensitization reaction.

FIG. 25 shows the examination results of the photosensitization effect caused by methylene blue using a He—Ne laser of 633 nm.

FIG. 26 shows the temporal variations of the backscattered light intensities for mixed solutions obtained by adding 20 μL of an o-PD/blue solution to each of glucose aqueous solutions having different concentrations, GOD and a HRP solution.

FIG. 27 is a diagram in which the peak time of the backscattered light intensity with respect to each glucose concentration is plotted.

FIG. 28 shows the temporal variations of the backscattered light intensities for mixed solutions obtained by adding an o-PD solution to each of ethanols having different concentrations, a HRP solution, and an AOD solution.

FIG. 29 is a diagram in which the peak time of the backscattered light intensity with respect to each ethanol concentration is plotted.

FIG. 30 (a) is a schematic diagram showing a measurement method in the ELISA method (Part 1), FIG. 30 (b) shows the relationship between the laser irradiation time and the backscattered light intensity, and FIG. 30 (c) shows the relationship between the time (predetermined time) required for the backscattered light intensity to decrease once and increase again to the initial intensity and the concentration of a HRP-labeled anti-IgG antibody.

FIG. 31 (a) is a schematic diagram showing a measurement method in the ELISA method (Part 2), FIG. 31 (b) shows the relationship between the laser irradiation time and the backscattered light intensity, and FIG. 31 (c) shows the relationship between the time (predetermined time) required for the backscattered light intensity to decrease once and increase again to the initial intensity and the concentration of HRP-labeled anti-IgG antibody.

FIG. 32 is a view showing a base plate having an antibody existing region A where an antibody exists and an antibody non-existing region B where no antibody exists.

FIG. 33 is a view showing a base plate with antibodies being immobilized by a doughnut-shaped porous support provided on the base plate.

FIG. 34 is a view showing a base plate with spacers being interposed between the porous support and the base plate.

FIG. 35 is a view showing a base plate on which the porous support is deformed in a convex shape.

FIG. 36 is a graph showing the results obtained by the conventional absorbance measurement method in the experiment described in 7-1.

FIG. 37 shows the results obtained by a method of the present invention in the experiment described in 7-1, wherein FIG. 37 (a) shows the relationship between the laser irradiation time and the backscattered light intensity, and FIG. 37 (b) shows the relationship between the peak time of the backscattered light intensity and the concentration of a HRP-labeled anti-IgG antibody.

FIG. 38 is a graph showing the results obtained by the conventional absorbance measurement method in the experiment described in 7-2.

FIG. 39 shows the results obtained by the method of the present invention in the experiment described in 7-2, wherein FIG. 39 (a) shows the relationship between the laser irradiation time and the backscattered light intensity, and FIG. 39 (b) shows the relationship between the time (predetermined time) required for the backscattered light intensity to decrease once and increase again to the initial intensity and the concentration of CRP.

FIG. 40 is a diagram illustrating the procedure of the experiment described in 7-3.

FIG. 41 shows the relationship between the peak time of the backscattered light intensity and the concentration of a HRP-labeled anti-IgG antibody in the experiment described in 7-3.

MODE FOR CARRYING OUT THE INVENTION

The inventors of the present invention made extensive studies to solve the above problems. As a result, the inventors have found that the predetermined object is achieved by conducting irradiation of light to (i) a polymerized substance obtained by generating a peroxide from a test substance and by bringing an oxidoreductase for producing a polymerized substance and a substrate of the oxidoreductase for producing a polymerized substance into contact with the peroxide; or (ii) a polymerized substance obtained by bringing a modifier in which a substance having a specific interaction with a test substance is modified with an oxidoreductase for producing a polymerized substance into contact with the test substance, and then bringing a peroxide and a substrate of the oxidoreductase for producing a polymerized substance into contact with the test substance, and by recording a temporal variation information of an intensity of scattered light generated from a irradiation point. Thus, the present invention has been completed.

In this specification, an "oxidoreductase for producing a polymerized substance", a "substrate of the oxidoreductase for producing a polymerized substance", a "polymerized substance", and a "polymer" are defined as follows.

First, the "oxidoreductase for producing a polymerized substance" is an enzyme for obtaining a polymerized substance by a polymerization reaction. Examples thereof include horseradish peroxidase (HRP) shown in the reaction formula described above and, in addition, peroxidase such as glutathione peroxidase and haloperoxidase. However, the present invention is not limited thereto, and the "oxidoreductase for producing a polymerized substance" may be any enzyme that oxidatively polymerizes a polymerizable substrate of the enzyme. Hereinafter, it may be often simply referred to as the "enzyme".

The above "substrate of the oxidoreductase for producing a polymerized substance" is a substrate for obtaining a polymerized substance by the above polymerization reaction. Examples thereof include phenylenediamine such as o-phenylenediamine (o-PD) and p-phenylenediamine (p-PD), which are aniline and its derivative; and phenolic compounds. Hereinafter, it may be often simply referred to as the "polymerizable substrate".

The above "polymerized substance" is obtained by a reaction of the oxidoreductase for producing a polymerized substance and the substrate of the oxidoreductase for producing a polymerized substance as described above. Examples thereof include dimers such as diaminophenazine (DAP).

The above "polymer" is formed when the polymerized substance absorbs light such as a laser light as shown in FIG. 1 and FIG. 2 described later. The polymer aggregated in a focused spot of light on a base (which is a polymer that scatters light) by the increase in polymerization degree of the above "polymer" is particularly referred to as a "nanostructure".

As described above, the measurement method of the present invention includes the following first method and the following second method.

(1) The First Method

A method for measuring a concentration of a test substance, the method comprising the steps of:
generating a peroxide from the test substance;
obtaining a polymerized substance by bringing an oxidoreductase for producing a polymerized substance and a substrate of the oxidoreductase for producing a polymerized substance into contact with the peroxide; and irradiating the polymerized substance with light to record a temporal variation information of an intensity of scattered light generated from an irradiation point.

(1) The Second Method

A method for measuring a concentration of a test substance, the method comprising the steps of:
obtaining a polymerized substance by bringing a modifier in which a substance having a specific interaction into contact with the test substance is modified with an oxidoreductase for producing a polymerized substance with the test substance, and then bringing a peroxide and a substrate of the oxidoreductase for producing a polymerized substance into contact with the test substance; and
irradiating the polymerized substance with light to record a temporal variation information of an intensity of scattered light generated from a irradiation point.

The first method and the second method are different in a process for obtaining a polymerized substance. That is, in the first method, using a test substance that produces a peroxide by a biochemical reaction such as enzyme reactions, a peroxide derived from the test substance is utilized to obtain a polymerized substance. In contrast, in the second method, a specific interaction with a test substance (e.g., antigen-antibody reaction) is utilized. The test substance used in the second method is not limited to the test substance that produces a peroxide used in the first method. The second method is useful as an alternative technique to the conventional ELISA methods.

According to the present invention, a test substance applicable to the above methods can be sensitively detected and quantified. Examples of the test substance include test substances detectable by the ELISA method (e.g., biological substances such as antibodies, influenza viruses, C-reactive proteins, plasma proteins, cytokines, DNA, peptides, and ligands; chemicals such as pesticide residues and environmental hormones contained in food; diagnostic substances such as blood sugar and tumor markers used for diagnosis of diabetes, cancers, or the like), in addition, biological substances such as glucose, cholesterol, and histamine; and substances that oxidize by an enzyme reaction such as ethanol and formic acids (and also including the above-mentioned glucose). Such various test substances can be sensitively detected and quantified.

Each step will be explained below.

First, a step of obtaining a polymerized substance will be explained in each of the first and second methods. The step of obtaining a polymerized substance is not intended to characterize the present invention, and a known method may be applied as long as it satisfies the following requirements.

(I) A step of generating a peroxide from the test substance, and a step of obtaining a polymerized substance by bringing an oxidoreductase for producing a polymerized substance and a substrate of the oxidoreductase for producing a polymerized substance into contact with the peroxide in the first method These steps are aimed at obtaining a polymerized substance by allowing an enzyme to react with the peroxide derived from the test substance and, for example, dimerizing the polymerizable substrate with the oxidation-reduction reaction of the enzyme.

The test substance used in the above method is not particularly limited as long as it generates a peroxide. Examples of the peroxide include inorganic peroxides such as hydrogen peroxide, sodium peroxide and the like, and organic peroxides such as benzoyl peroxide, cumene hydroperoxide and the like. The peroxide can be obtained, for example, by an enzyme reaction when an enzyme is added to the test substance. As examples of the test substance, glucose, ethanol, cholesterol, formic acid, or the like can be given. For example, when using a peroxide-generating substance such as glucose that is oxidized with an oxidase (a glucose oxidase in the case of using glucose) as a test substance, hydrogen peroxide produced by a reaction of glucose with a glucose oxidase reacts with an oxidoreductase for producing a polymerized substance and a substrate for an oxidoreductase for producing a polymerized substance as shown in the reaction formula described above. Of course, the present invention is not limited thereto.

(II) A step of obtaining a polymerized substance by bringing a modifier in which a substance having a specific interaction with the test substance is modified with an oxidoreductase for producing a polymerized substance into contact with the test substance, and then bringing a peroxide and a substrate of the oxidoreductase for producing a polymerized substance into contact with the test substance in the second method As described above, the second method is common to the first method in that the polymerizable substrate is converted to a polymerized substance with the oxidation-reduction reaction of an enzyme. However, as the premise, the second method differs from the first method in that rather than using a peroxide derived from the test substance as in the first method, the test substance and a modifier in which a substance having a specific interaction with the test substance is modified with an oxidoreductase for producing a polymerized substance are mixed, a peroxide and a polymerizable substrate are added to the resulting substance, and the resulting mixture is used.

Here, the above "specific interaction with the test substance" includes, for example, an antigen-antibody reaction. The above "substance having a specific interaction with a test substance" includes, for example, an antibody or antigen against the test substance. The above "modifier in which a substance having a specific interaction with the test substance is modified with an oxidoreductase for producing a polymerized substance" includes an antibody or antigen labeled with an oxidoreductase or the like, against the test substance.

When the above "specific interaction with a test substance" is an antigen-antibody reaction, for example, all of the various methods (the direct absorption method, the competitive method, the sandwich method, etc. as described above) used in the ELISA method may be applied. For more information on the ELISA method, it can be referred to, for example, such a literature as Medical & Biological Laboratories, Measurement Principle ELISA Method (2011).

Specifically, for example, an antibody (primary antibody) against the test substance may be allowed to react with an antibody labeled with an oxidoreductase for producing a polymerized substance and sequentially react with a substrate of the above enzyme. Here, the above "antibody labeled with an oxidoreductase for producing a polymerized substance" means, as a result, an antibody to be labeled with the above enzyme. Therefore, when used, the antibody may be labeled directly with enzyme, and may not be labeled. Since the former oxidoreductase-labeled antibodies are expensive, like the cases of the latter, the antibody may be allowed to react with the oxidoreductase at the time of use, and the antibody labeled with the above oxidoreductase may be used. Moreover, the above enzyme may be covalently bound to an antibody or antigen against the test substance. Alternatively, an antibody (secondary antibody) that recognizes the antibody (primary antibody) against the test substance or an antigen may be further labeled with the enzyme.

(III) A step of irradiating the polymerized substance with light to record a temporal variation information of an intensity of scattered light generated from an irradiation point (the common step to the first method and the second method) The above step will be described in detail below. First, the polymerized substance is irradiated with light. Irradiation of light allows oxidative polymerization to proceed, and the polymerized substance absorbs light to form a polymer, thereby enhancing the polymerization degree. The polymer is aggregated in the focused spot on a light-transmitting base to form a nanostructure (a polymer that scatters light). The above-mentioned scattered light includes also a reflected light, backreflected light and backscattered light. As the above light, a laser light is preferably used in order to accurately measure the change in intensity of scattered light. Furthermore, when being irradiated with light, it is preferred that light be focused on the interface between a base such as a glass plate and a solution containing a polymerized substance derived from a test substance.

In the present invention, it is preferred that the temporal variation information constitute a signal waveform, and the method further comprise the step of identifying a time taken from a predetermined time point on and after a start of the light irradiation to the test substance until the signal waveform shows an extremum.

Hereinafter, the above steps that characterize the present invention will be described with reference to FIGS. 1 and 2. FIGS. 1 and 2 show examples using a HRP as the oxidoreductase for producing a polymerized substance, hydrogen peroxide as the substrate of the HRP, o-PD as a chromogenic substrate of the oxidoreductase, and a laser light as the light. However, the present invention is not intended to be limited thereto.

FIG. 1 schematically shows a state in which the polymerized substance (DAP) produced by a series of reactions used for the detection of β-D-glucose as described above is irradiated with a laser light to produce a polymer aggregate of o-PD. As shown in FIG. 1, in the conventional method, the absorbance of the DAP (dimer) of polymerized substance generated by the oxidation reaction of o-PD has been measured by using a spectrometer, and the concentration of the test substance has been quantified. In contrast, in the present invention, the DAP is irradiated with a laser light to progress an oxidative polymerization reaction, and the temporal variation information of the intensity of scattered light generated from the irradiation point of the produced polymer aggregate (nanostructure) is recorded. The temporal variation information includes, for example, the peak time required for obtaining the peak intensity of the scattered light, the time taken from a predetermined time point on and after the start of the light irradiation until a signal waveform shows an extremum, and the like. According to the present invention, quantitative measurement of the concentration of a test substance can be rapidly and sensitively performed compared with conventional methods.

As a laser light used in the above steps, a laser in the visible light region is preferably used from the viewpoint of measurement sensitivity. For example, a green laser with a wavelength of 500 to 550 nm is preferably used. However, by using a photosensitizer such as methylene blue, porphyrin-based dyes, or the like, it is also possible to use a laser in a longer wavelength region (e.g., a red laser having a wavelength of 600 to 700 nm). As a result, the practicality such as enlargement of the range of usable measurement wavelengths improves.

A reaction mechanism inferred in the present invention will be described in more detail with reference to FIG. 2. FIG. 2 shows an example using a light-transmitting base and a sample solution containing the test substance (specifically, a solution that containing HRP, o-PD that is a chromogenic substrate of HRP, and hydrogen peroxide).

First, a predetermined amount of the above sample solution is added dropwise onto the above base (see (i) of FIG. 2). As a result, by the oxidative polymerization reaction of HRP, the o-PD changes to 2,3-diaminophenazine (DAP), which is a dimer, having light absorbing property. Next, when the DAP is irradiated with a laser light, and the light is focused on the base plate, a reactive oxygen species having a strong oxidizing power is generated by light absorption of the DAP (see (ii) of FIG. 2). Due to a strong oxidizing power of the reactive oxygen species thus generated, the oxidative polymerization reaction by HRP is further accelerated, and the polymer aggregate of o-PD is formed at the focused spot of the laser light, (see (iii) of FIG. 2). Note that although the structure of the polymer aggregate of o-PD is shown in (iii) of FIG. 2, this structure is only an example of an expected structure, and it is not intended to be limited thereto. The polymer aggregate of o-PD thus obtained changes the intensity of scattered light generated from the irradiation point (focal spot) of reflected laser light. The intensity of the scattered light is measured and the temporal variation information of the intensity of the scattered light generated from the irradiation point is recorded. As one example of the temporal variation information of the intensity of the above scattered light, for example, a peak time required for obtaining a peak intensity can be given. As demonstrated in the Examples below, because the peak time has a good correlation with the concentration of an o-PD solution, hydrogen peroxide, or the like, it is assumed that the test substance in the sample solution can be quantitatively detected with high sensitivity by measuring the above peak time.

Here, the "peak intensity" includes both extremums of a maximum value and a minimum value. The reason is that, as shown in experimental examples as described later, both the extremums can be obtained depending on the composition of a sample solution containing a test substance, the concentration of a test substance, and the like. The peak intensity may be a first peak intensity and may be any peak intensity such as a second one, a third one or the like. Furthermore, because a signal always contains noise, the extremums, for example, within ±10% (more preferably within f7%, further preferably within ±5%) of the scattering intensity at the start of the irradiation of laser light may be excluded from the extremums in the present invention. As a method for determining a position of an extremum, for example, when differentiating a graph of the temporal variation information of scattered light intensity, the position may be identified as a portion where the differential value that has been a negative value in a predetermined interval (e.g. 5 bits) shifts to a positive value in a predetermined interval (e.g. 5 bits).

Next, a detection apparatus according to the present invention will be explained. The detection apparatus of the present invention is characterized by including a light source that allows light to enter a test substance, a photoelectric conversion element that detects scattered light generated from a polymerized substance derived from the test substance, and a recording medium that continuously records a signal output from the photoelectric conversion element during a predetermined period of time. The detection apparatus of the present invention is preferably an apparatus to detect a test substance present on the first surface side of a light transmitting base, and includes a lens facing the second surface side of the light transmitting base, a laser light source that allows light to enter the light transmitting base through the lens, a photoelectric conversion element to detect light scattered from a polymerized substance derived from the test substance present on the first surface side of the light transmitting base through the lens, and a medium to continuously record a signal output from the photoelectric conversion element during a predetermined period of time. Note that a test substance in the detection apparatus of the present invention is not limited to the test substance used in the first and second methods and means a substance from which a polymerized substance derived from the test substance can be obtained by absorbing light.

The light transmitting base means an object that can transmit light, and can transmit preferably 85% or more, more preferably 90% or more, further preferably 95% or more of light having a wavelength of 532 nm. Specifically, as examples thereof, a glass plate, plastic and the like can be given. The shape of the light transmitting base is preferably a flat plate shape. The reason therefor is that a reduction in the detection amount of light due to scattering and refraction by the light transmitting base itself is avoided as much as possible because a test substance is detected based on the intensity of the scattered light generated from the test substance present on the first surface side of the light transmitting base in the present invention. The light transmitting base preferably has a small thickness, and for example, it is preferably 0.5 mm or less, more preferably 0.2 mm or less. Although there is no particularly preferred lower limit of the thickness of the light transmitting base, it is, for example, 0.05 mm or more, preferably 0.1 mm or more in order to function to hold the test substance. There is no particular limitation on the wavelength and the intensity of a laser light as long as it promotes the polymerization of a polymerized substance. As the photoelectric conversion element, it is possible to use a photomultiplier, a photodiode, a phototransistor, a solid-state imaging element, or the like. As the medium to continuously record a signal output from the photoelectric conversion element during a predetermined period of time, any recording medium can be used regardless of volatile or nonvolatile, and examples thereof includes various flash memories, hard disks or DRAMs built in personal computers, SRAMs or the like.

The detection apparatus of the present invention may further include a calculating means that identifies a time taken from a predetermined time point on and after the start of laser light irradiation to a test substance until the signal waveform recorded in the recording medium shows an extremum. In order to obtain an extremum of the signal waveform, for example, a photoelectric conversion element having one pixel unit is used to obtain a single signal waveform, and an extremum may be identified from the single signal waveform. Alternatively, a photoelectric conversion element such as a solid-state imaging element, which is an image sensor having a plurality of pixel units, is used to once obtain a signal waveform for each pixel, a single signal waveform is obtained for example by calculating an average value of these signal waveforms, and an extremum may be identified from the single signal waveform.

Note that the reason for identifying a time taken from a predetermined time point on and after the start of irradiation is that this also makes it possible to remove a part of data in a period when signal waveforms are unstable immediately after the start of irradiation. Of course, "on and after the start of irradiation" is intended to include "at the start of irradiation". The time calculating means for calculating a time required from the start of the irradiation of laser light to the light transmitting base until an output signal of the photoelectric conversion element indicates an extremum may be realized by hardware, and however, it is preferred to implement by processing on software.

As for light scattered from the test substance, it is preferred to use a backscattered light. The reason therefor is that at least part of an optical system for allowing laser light to enter a test substance and an optical system for detecting light scattered from the test substance can be shared, which is useful in a reduction in size of a whole apparatus.

Hereinafter, using the detection apparatus of FIG. 3, which is one embodiment of the present invention, the measurement methods of the present invention will be described through various basic experiments and embodiments in further detail.

In the following description, there is a case of using the abbreviations listed below.

o-phenylenediamine (substrate of oxidoreductase): o-PD 2,3-diaminophenazine (a polymerized substance): DAP polyphenylenediamine: polymer glucose oxidase: GOD horseradish peroxidase (oxidoreductase): HRP alcohol oxidase: AOD Note that since o-PD has a very strong oxidizing power and is readily oxidized naturally, the o-PD solution used in the experiment contains a small amount of DAP resulting from natural oxidation.

1. REAGENT AND MEASUREMENT APPARATUS USED IN THE EXPERIMENT

1-1. Reagent o-phenylenediamine (Wako)

glucose oxidase (162 unit/mg, TOYOBO)

horseradish peroxidase (100 unit/mg, Wako)

methylene blue (Wako)

These reagents were dissolved in a citrate buffer (pH: 4.6) as a solvent so as to have respective predetermined concentrations.

alcohol oxidase (*Pichia pastoris*, 38 unit/mL, SIGMA-ALDRICH)

etanol (99.5%, Wako)

1-2. Preparation of a Base Plate

A micro cover glass 17 (size: 24 mm×36 mm; thickness: 0.12 to 0.17 mm, MATSUNAMI) was washed with a detergent (decon 90, Decon Laboratories Limited) and dried, and a silicon sheet 15 (thickness: 0.2 mm, Asone) having 9 to 12 holes with a diameter of 3.5 mm formed with a punch was placed on the micro cover glass to prepare a multiwell base plate (hereinafter, may often be referred to as the base plate) as shown in FIG. 4. In the figure, a 16 is a solution to be measured.

1-3. Measurement of Backscattered Light Intensity Using a Laser Condenser

1-3-1. Measurement Apparatus

A schematic view of a laser condenser used in the present experiment is shown in FIG. 3. As a laser light source 1, a DPSS laser (SDL-473-050TL, Shanghai Dream Lasers Technology) with a wavelength of 473 nm, a YAG laser (SDL-532-020TL, Shanghai Dream Lasers Technology) with a wavelength of 532 nm, and a He—Ne laser (31-2066-000, COHERENT) with a wavelength of 633 nm were used. Laser light was expanded with a beam expander 2, and then introduced through a ND filter 3 into an inverted microscope 5 (IX70-S1F2, OLYMPUS). The laser light was reflected by a half mirror 6 (reflection: 70%) and focused on the upper surface (an interface between a base plate and a solution) of a base plate 9 placed on a stage 8 of the inverted microscope using an objective lens 7 (UPlanFL N, 60×, OLYMPUS). A nanostructure 10 of polymer was formed at the focused spot. The laser intensity at the focal point of each laser light source is shown in Table 1. A backscattered light passes through an optical fiber 12 via a coupler 11 and is detected by a photomultiplier tube 13 (Hamamatu Photonics, R1166), and after being converted into an electrical signal, the electrical signal is output to a computer (PC) via an expansion board for storing data 14. A mechanical shutter 4 capable of controlling opening and closing by an external input was placed on an optical path of laser so as to be automatically controlled by a program from the computer.

TABLE 1

| wavelength of laser light source | laser intensity at the focal point |
|---|---|
| 473 nm | 0.09 mW |
| 532 nm | 2.25 mW |
| 633 nm | 1.8 mW |

A green LED (M530L2, wavelength: 530 nm; intensity: 220 mW, Thorlabs) was used for coloring the o-PD by light irradiation.

1-3-2. Measurement Procedure of a Backscattered Light Intensity

The base plate 9 was fixed on the stage of the inverted microscope 5, and in order to focus a laser light on the upper surface of the base plate, the height of the objective lens 7 was adjusted such that a diameter of a focused spot of the laser light reflected by the upper surface of the base plate becomes small. The shutter 4 was closed to block the laser light, and then 10 to 20 μL of a sample solution containing o-PD was added dropwise to each well of the base plate 9. By setting a measurement rate of voltage output from the photomultiplier 13 to be 50 Hz and the number of measurement points to be 3000 to 15000 by a program, a measurement time was adjusted from 1 to 5 minutes. When the shutter 4 was opened by operating the computer, laser was focused on the sample, and the measurement of the backscattering light intensity accompanied by the formation of a polyphenylenediamine nanostructure was started. The mechanical shutter 4 was automatically closed when a set time elapsed, and the measurement was completed.

1-4. Measurement Procedure of an Absorption Spectrum

For Comparison

For comparison, an absorption spectrum of DAP (dimer) produced by oxidation of o-PD was measured with a spectrophotometer. The measurement of the absorption spectrum was performed using a spectrophotometer (UV-2550, SHIMADZU). A sample and pure water for comparison was each placed in a measurement cell (10×10×45 mm, Dispocell UV, Nikko Hansen Co., Ltd.) and the cells were set in the spectrophotometer. In a wavelength range of 300 to 900 nm, a sampling pitch was set to 0.5 nm, and a scanning speed was set to a high speed, and thus the absorption spectrum of the sample was measured.

1-5. Observation of Polymers by a SEM

The polymer formed on the base plate was observed using a scanning electron microscope (hereinafter, may often be referred to as SEM) (FEI, DB-235). A SEM is one of electron microscopes capable of observing a sample by irradiating the sample to be measured with focused electron beam and detecting secondary electrons emitted from the sample. Since the SEM irradiates a sample with an electron beam, the surface of the sample is required to be conductive. Therefore, using a neo osmium coater (Meiwafosis Co., Ltd, NeoC-ST) in this experiment, an osmium metal conductive film was deposited on the surface of the base plate for approximately 2.5 nm to impart conductivity to the surface, and a measurement was then conducted by the SEM.

2. OXIDATIVE POLYMERIZATION REACTION OF O-PD BY LASER IRRADIATION

Here, it is shown that instead of using the HRP enzyme reaction, o-PD is irradiated with a green LED to form DAP, and a nanostructure that is a polymer aggregate can be obtained by light absorption of DAP contained in the o-PD solution.

2-1. Change in Absorption Spectrum and Change in Backscattered Light Intensity by Irradiating o-PD with a Green LED An o-PD solution (0.33 mM) was placed in a measurement cell of a spectrometer and irradiated with a green LED of 200 mW/cm² (wavelength: 530 nm) during a predetermined period of time, followed by measuring the absorption spectrum of the o-PD solution at each irradiation time with the spectrophotometer. The resulting absorbance spectra are shown in FIG. 5 (a). As shown in this figure, as the irradiation time of the green LED becomes longer, the absorbance of the light absorbance spectrum having a peak at a wavelength of about 450 nm increased. The shape of this absorption spectrum conforms to the shape of the absorption spectrum of DAP that is a dimer of o-PD. That is, it was confirmed that DAP was produced by oxidation of the o-PD solution and the color changed to orange.

Next, 20 μL each of the o-PD solutions having different LED irradiation times was collected from the measurement cell of the spectrometer, and added dropwise onto the base plate of the laser condenser, and a laser light was focused on the solution to measure a backscattered light intensity for 60 seconds. The temporal variations of the obtained backscattered light intensities are shown in FIG. 5 (b). It was confirmed from this figure that as the LED irradiation time becomes longer, the time (peak time) required for the backscattered light intensity to reach a maximum is shortened. This shows that if the DAP concentration of the o-PD solution is increased, a time required for a nanostructure to grow to a certain height is shortened. Although laser was focused on the o-PD solution that had not been irradiated with LED, the backscattered light intensity did not change. It is assumed from this that the polymerized substance in the o-PD solution is important for the formation of nanostructures.

FIG. 6 is a graph in which the peak time of the backscattered light intensity with respect to the peak absorbance is plotted. It is understood from this figure that the peak time of the backscattered light intensity is shortened with an increase of the absorbance when the o-PD solution is oxidized.

2-2. Temporal Variations of Backscattered Lights and SEM Photographs

Each of three kinds of o-PD aqueous solutions of 0.2 mM, 1 mM and 4 mM was added dropwise onto the above base plate and irradiated for 80 seconds by focusing a green laser light having a wavelength of 532 nm and an intensity of 2 mW, and the backscattered light intensity was measured to examine the temporal variation. The results are shown in FIG. 7 (a). As shown in FIG. 7 (a), the higher the concentration of the o-PD aqueous solution, the earlier the time when the backscattered light intensity first reaches a maximum (a peak time required for a first peak intensity to be obtain).

Furthermore, after the laser irradiation, a SEM image of polymer formed at the focused position on the base plate was measured. FIG. 7 (b) shows SEM photographs of the o-PD aqueous solutions having different concentrations after being irradiated with a green laser light for 80 seconds. It can be seen from FIG. 7 (b) that the structure of the polymer is formed at the position of the focused spot. The higher the concentration of the o-PD aqueous solution, the larger the size of the polymer. This is because the higher the concentration of the o-PD aqueous solution, the faster the formation rate of a nanostructure. Note that when the o-PD aqueous solution had the concentration of 4 mM, a structure having a distorted shape was formed. This seems to be the cause for the discontinuous temporal variation of backscattered light intensity at around 50 seconds as shown in FIG. 7 (a) described above.

2-3. Optical Micrographs of Change in Backscattered Light Intensity

FIG. 8 (a) to 8 (f) are photographs of the images of the reflected light obtained by focusing a green laser on an o-PD solution of 1 mM, taken every 4 seconds using a CCD camera fitted with an optical microscope. The green spot in the center is a reflected light from the laser focal point. It can be seen that the backscattered light intensity increases from FIG. 8 (a) to FIG. 8 (d) and then decreases from FIG. 8 (d) to FIG. 8 (0.

2-4. Relationship Between the Temporal Variation in Backscattered Light Intensity and the Height of a Polymer Here, the relationship between the temporal variation in backscattered light intensity and the height of a nanostructure to be formed was examined. The measurement procedure of this experiment is shown in FIG. 9 (a).

Specifically, an o-PD aqueous solution of 1 mM was irradiated with a green laser of 200 mW/cm² (wavelength: 532 nm) for about 10 minutes to prepare an o-PD solution containing DAP. 20 μL of the o-PD solution thus obtained was added dropwise onto a base plate, a laser light was focused on the solution, and the temporal variation in the reflected light intensity was measured for 20 seconds. The same experiments were conducted by changing the irradiation time of the laser light, and the shape of a nanostructure formed at the laser light focused position on the glass plate in each laser irradiation time was observed with an atomic force microscope (hereinafter, may often be referred to as an AFM) (SII, SPI-4000). The measurement of the AFM was performed in tapping mode using a Si cantilever.

FIG. 9 (b) shows AFM observation images when irradiated with laser from 4 seconds to 16 seconds. It can be seen from this figure that when the laser irradiation time increases, the nanostructure increases in size and grows.

FIG. 9 (c) is a graph in which the laser irradiation time on the horizontal axis, the backscattered light intensity on the left vertical axis, and the height of the nanostructure on the right vertical axis are plotted. A time required for the backscattered light intensity to first reach a maximum (a first peak time) represents a time required for the polymer to grow to a certain height. It can be seen from this figure that when the backscattered light intensity reaches a maximum, the height of the nanostructure becomes 80 nm, and when the backscattered light intensity takes a minimum, the height of the nanostructure grows to 180 nm.

As shown in FIG. 10, the light being detected in the present invention is a superimposed light of a reflected light of the focused laser reflected by the interface between the base plate and the nanostructure, and a reflected light of the focused laser reflected by the interface between the structure and the solution. Therefore, the phase of light changes with the growth of the nanostructure. When the phases of two waves match, the backscattered light intensity reaches a maximum, and when the phase is shifted by half a wavelength, the backscattered light intensity becomes a minimum. Then, it is considered that the backscattered light intensity increases again by further phase change.

2-5. Simulation of Reflectance

Here, in order to illustrate the mechanism of the temporal variation in the backscattered light intensity, a calculation was performed based on the Fresnel equation for a model system.

A model sample (a polymer thin film sandwiched between a glass plate (refractive index: 1.52) and water (refractive index: 1.33)) as shown in FIG. 11 (a) was prepared, and the reflectance obtained when light having a wavelength of 532 nm is allowed to enter from the glass plate side was calculated using the complex refractive index and the thickness of the polymer thin film as parameters. The relationship between the film thickness and the reflectance for the cases of the complex refractive index of the polymer thin film being set to 1.7-0.2 i, 1.6-0.2 i and 1.5-0.2 i is shown in FIG. 11 (b).

As is understood from the above figure that the reflectance is repeatedly increased and decreased with an increase in thickness of the polymer thin film. This is due to the interference of the lights reflected by the two interfaces of the polymer thin film. Under the above calculation conditions, the reflectance reaches a maximum at the film thickness of around 70 to 100 nm and around 240 to 290 nm and becomes minimum at the film thickness of around 160 to 200 nm, which is similar to the results of the experiment in which the relationship between the height of the polymer and the laser irradiation time was examined. That is, it can be seen that the temporal variation in the backscattered light intensity in this experiment is due to the growth of a nanostructure formed on the focused laser spot. The smaller the real part of the refractive index, the larger decrease in reflectance is observed when the thickness of the polymer thin film increases from 0.

2-6. Relationship Between a DAP Concentration and the Peak Time of a Backscattered Light Intensity Here, the relationship between a DAP concentration and the peak time of a backscattered light intensity was examined. The measurement procedure of this experiment is shown in FIG. 12 (a).

Specifically, each of DAPs of 0 to 750 μM (more specifically 0 M, 75 μM, 750 μM, 75 nM, 7.5 mM and 750 mM) was added to an o-PD solution of 1 mM, and a total of six types of mixed solutions were prepared. 20 mL of each mixed solution was added dropwise onto a base plate, and a laser light of 2 mW was focused thereon with an objective lens to measure the temporal variation in backscattered light intensity. The results are shown in FIG. 12 (b). It can be seen from this figure that the higher the concentration of DAP, the earlier the time (peak time) required for the backscattered light intensity to first reach a maximum appears.

The relationship between the concentration of DAP and the peak time of the backscattered light intensity is shown in FIG. 12 (c). It was confirmed from this figure that both have a good correlation, and the concentration of DAP can be quantitatively measured by detecting the peak time required for the backscattered light intensity to first reach a maximum.

As described above, when o-PD is oxidized by an enzyme reaction using a HRP and hydrogen peroxide, DAP that is a polymerized substance (dimer) is produced. When hydrogen peroxide and o-PD are mixed in each of solutions having different HRP concentrations at a constant concentration, DAP is produced in proportion to the HRP concentration. Therefore, a HRP concentration can be also measured similarly by focusing laser light and measuring the temporal variation in the backscattered light intensity. This shows that the method of the present invention is applicable to the ELISA method.

3. PROMOTION OF OXIDATIVE POLYMERIZATION REACTION OF O-PD BY ENZYME REACTION

Here, it will be described that an oxidative polymerization reaction of o-PD is promoted by an enzyme. When laser is focused on a base plate, a reactive oxygen species is generated by the light absorption of DAP obtained by an oxidative polymerization reaction with an enzyme. Oxidative polymerization proceeds due to a strong oxidizing power of the reactive oxygen, and a nanostructure that is a polymer aggregate is formed at the focal point. The nanostructure changes the reflected laser light intensity.

3-1. Promotion of an Oxidative Polymerization Reaction by an Enzyme Reaction

20 μL each of a HRP solution, hydrogen peroxide (0 to 200 μM) and an o-PD solution (1 mM) were collected and mixed in a microtube, 20 μL of the resulting mixed solution was added dropwise onto a base plate to measure a backscattering light intensity. The following shows the oxidative polymerization reaction [o-PD→DAP→Poly (OPD) (=polymer)] of o-PD by a HRP enzyme reaction.

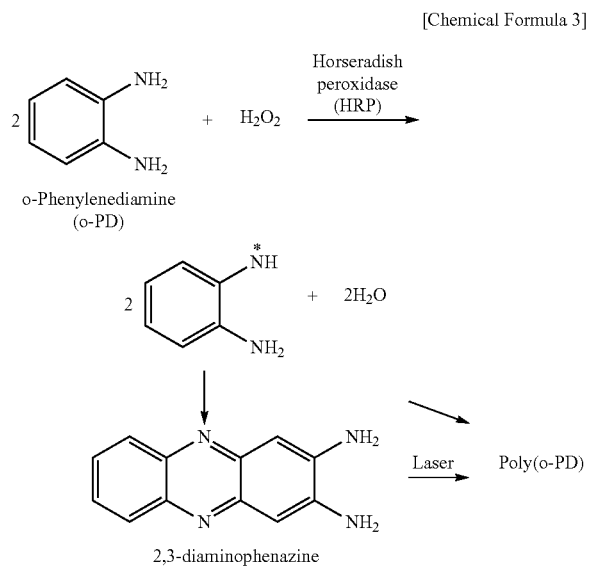

[Chemical Formula 3]

The temporal variations in the backscattered light intensity thus obtained are shown in FIG. 13 (a). It is understood from this figure that as the concentration of hydrogen peroxide increases, the peak (maximum value) of the backscattered light intensity increases, and the peak time is shortened.

A graph in which the peak time of the backscattered light intensity with respect to the concentration of hydrogen peroxide was plotted is shown in FIG. 13 (b). It is confirmed from this figure that it is possible to quantify hydrogen peroxide at a concentration range of 3.1 to 200 μM by the above method. This is because o-PD is oxidized by HRP and hydrogen peroxide, thereby producing DAP.

This result shows that the formation rate of the nanostructure obtained as described above is accelerated by the oxidation reaction by the enzyme and can be detected as a temporal variation in backscattered light.

3-2. SEM Observation of a Polymer by an Enzyme Reaction

20 μL each of an o-PD solution (0.33 mM), an o-PD solution (1 mM), a HRP solution, and a hydrogen peroxide (0.2 mM) were mixed, 20 μL of the resulting mixed solution was added dropwise onto a base plate, and a laser light was focused on the solution for two minutes to conduct the SEM observation of a nanostructure formed on the focal point. For comparison, laser light is focused only on the o-PD solution to conduct the SEM observation likewise.

FIG. 14 (a) shows SEM observation images when using only the o-PD solution, and FIG. 14 (b) shows SEM observation image when the HRP solution and the hydrogen peroxide were added to the o-PD solution. In each figure, the view on the left side shows a view of the nanostructure as measured from above, and the view on the right side is a 45 degrees tilted view of the nanostructure. It is confirmed from the SEM observation images of FIG. 14 (b) that the formation rate of polymer was accelerated by the enzyme reaction, and the polymer having a larger size was formed. From the above results, it can be seen that the promotion of the oxidative polymerization reaction by the enzyme occurs in a height direction rather than in a diameter direction. The reason therefor is presumed that the above oxidative polymerization reaction progresses within a laser focused spot.

The present application claims the benefit of priority based on Japanese Patent Application No. 2013-218750 filed on Oct. 21, 2013 and priority based on Japanese Patent Application No. 2013-219688 filed on Oct. 22, 2013. The entire contents of the specification of Japanese Patent Application No. 2013-218750 filed on Oct. 21, 2013 and that of the specification of Japanese Patent Application No. 2013-219688 filed on Oct. 22, 2013 are incorporated herein by reference.

4. DETECTION OF GLUCOSE 4-1. Quantitative Determination of Glucose Concentration The measurement procedure of this experiment is shown in FIG. 15 (a). Specifically, 20 μL of a glucose aqueous solution (0 to 1 mM) and 20 μL of a solution obtained by mixing GOD and HRP in a ratio of 1:1 (hereinafter, abbreviated as GOD/HRP) were mixed and allowed to stand at a constant temperature for one minute. 20 μL of an o-PD solution (1 mM) was added thereto, and 20 μL collected from the resulting mixed solution was added dropwise onto a base plate to measure the backscattered light intensity. Similarly, the backscattered light intensities were measured using a ribose solution and a lactose solution (5 mM) having no activity against GOD as a control.

The temporal variations in the backscattered light intensities obtained are shown in FIG. 15 (b). The higher the concentration of glucose, the earlier the maximum of the backscattering light intensity (a first peak intensity) appeared.

A graph in which the time when the first peak of the backscattered light intensity appeared with respect to each of the glucose concentrations is plotted is shown in FIG. 15 (c). It was confirmed from this figure that the clear correlation between both can be seen, and glucose can be quantified in the concentration range of 100 nM to 1 mM. The reason therefor is considered that the formation rate of the polymer of o-PD is dependent on the glucose concentration and hence the glucose concentration can be quantified from the temporal variation in the backscattered light intensity. On the other hand, when the reflected light intensities were similarly measured using ribose and lactose (5 mM) as a control instead of glucose, the peaks of the backscattered light intensities appeared at almost the same time as in the glucose concentration of 100 nM. The reason therefor is considered that GOD has a slight activity against ribose and lactose.

It was confirmed from the above results that, according to the present invention, the concentration of glucose can be specifically measured with high sensitivity (detection sensitivity: 100 nM to 1 mM) utilizing the specificity of GOD.

4-2. Comparison with a Conventional Glucose Detection Method

Spectrophotometric Method

The measurement procedure of this experiment is shown in FIG. 16 (a). Specifically, 300 μL of each of glucose aqueous solutions (0 to 1 mM) and 300 μL of a GOD/HRP solution were mixed in a measurement cell of a spectrophotometer, and allowed to stand at a constant temperature for one minute. 300 μL of an o-PD solution (1 mM) was added thereto and mixed to measure the absorption spectrum with the spectrophotometer. The absorption spectra obtained are shown in FIG. 16 (b). Further, a graph in which the peak absorbance with respect to each glucose concentration was plotted is shown in FIG. 16 (c).

As a result, the differences in absorbance were observed between the glucose concentrations of 1 mM, 100 μM, and 10 μM. That is, in the absorption spectrum measurement that is a conventional glucose detection method, glucose was able to be detected in a concentration range of 100 μM to 1 mM. The same measurements of the reflected light intensity were conducted using ribose and lactose (5 mM) instead of glucose, and as a result, the same results as in the cases of glucose concentrations of 10 μM or less were obtained.

It was confirmed from these results that, according to the present invention, glucose can be detected at 1000 times more sensitive compared with the conventional method.

A comparison of the method of the present invention and the conventional method is shown in Table 2. The detection method of glucose according to the present invention is extremely superior to the conventional method in that a necessary amount of a sample is small and the detection sensitivity is high.

TABLE 2

|  | a necessary amount of a sample | glucose detection sensitivity |
| --- | --- | --- |
| the method of the present invention | 20 μL or less | 100 nM~1 mM |
| the conventional method | 1 mL or more | 100 μM~1 mM |

Furthermore, a comparison with a glucose detection method using a commercially-available glucose assay kit (Glucose kit: Glucose CII-Test Wako, Wako Pure Chemical Industries, Ltd.) using a colorimetric method was conducted. The results of the comparison with the method of the present invention for a temperature, a measurement time, a necessary amount of a sample, and glucose detection sensitivity are shown in Table 3. As shown in this table, in the measurement using the commercially-available glucose assay kit, heating to 37° C. is necessary and it takes 5 minutes or longer for measuring. Furthermore, glucose concentrations in a range of 200 μM to 39 mM can be detected using 200 μL of a sample. In contrast, according to the method of the present invention, the measurement can be conducted at room temperature without a need for heating and takes only about 1 to 2 minutes from the start of measurement. Moreover, according to the method of the present invention, glucose concentrations of 100 nM to 1 mM can be quantified using 20 μL or less of a sample. Therefore, it was found that, according to the present invention, glucose can be quantified rapidly and with high sensitivity as compared with the case of using a commercially-available kit.

TABLE 3

|  | temperature | measurement time | a necessary amount of a sample | glucose detection sensitivity |
| --- | --- | --- | --- | --- |
| the conventional method | heating to 37° C. | ≥5 min | 200 μL | 200 μM~39 mM |
| the method of the present invention | room temperature (25° C.) | 1-3 min | ≤20 μL | 100 nM~1 mM |

4-3. Laser Wavelength Dependence of Glucose Detection Sensitivity

Using laser light sources respectively having a wavelength of 473 nm, 532 nm and 633 nm, the backscattering light intensities in the detection of glucose were measured to examine the dependence on a laser wavelength. The temporal variations of the backscattered light intensities obtained are shown in FIG. 17 (wavelength: 473 nm), FIG. 18 (wavelength: 532 nm), and FIG. 19 (wavelength: 633 nm). Furthermore, the peak time of the backscattered light intensity with respect to the glucose concentration at each of the above-mentioned wavelengths is further shown in FIG. 20. It was confirmed from these figures that glucose concentrations in a range of 1 μM to 1 mM can be quantified in the case of a wavelength of 473 nm, glucose concentrations in a range of 100 nM to 1 mM can be quantified in the case of a wavelength of 532 nm, and glucose concentrations in a range of 0.5 mM to 2.5 mM can be quantified in the case of a wavelength of 633 nm. Therefore, it was found that a green laser light having a wavelength of 532 nm is most suitable for the detection of glucose under the conditions of this experiment.

4-4. Relationship Between the Absorption Spectrum of an o-PD Solution and the Backscattered Light Intensity Spectrum of a Polymer Here, the relationship between the absorption spectrum of an o-PD solution and the backscattered light intensity spectrum of a polymer was examined.

The absorption spectrum of the o-PD solution (3.8 mM) used in this experiment is shown in FIG. 21. As shown in this figure, the absorption spectrum of the o-PD solution has a peak at a wavelength of around 450 nm, and the absorbance at each laser wavelength was 0.056 (wavelength: 473 nm), 0.017 (wavelength: 532 nm), and 0.007 (wavelength: 633 nm). It is considered that since DAP formed by natural oxidation due to oxygen in the air was contained in the o-PD solution, the absorption spectrum of the DAP having a peak at around 450 nm was obtained.

FIG. 22 shows the absorption spectrum of the above o-PD solution (left axis) and the spectrum of the backscattered light intensity of a nanostructure (right axis) formed by dropping the above o-PD solution onto a base plate and focusing laser having a wavelength of 532 nm thereon. The nanostructure formed by the above process had a size of nano level of 1 μm or smaller, and the absorption spectrum thereof was not be able to be measured. Therefore, the scattering spectrum was measured by irradiating a halogen lamp using a dark field condenser lens.

The nanostructure formed at the focal point has a scattering peak at about 620 nm, which is in a longer wavelength side than a wavelength of the peak of the absorption spectrum of the dimer (DAP) in the o-PD solution. Since the scattering spectrum of fine particles provides the same information as the absorption spectrum, it can be confirmed from the results of the above scattering spectrum that the formed nanostructure strongly absorbs light of a longer wavelength region than a region of light that DAP absorbs. The reason therefor is considered that a π-electron conjugated length elongates due to the polymerization of o-PD, and the absorption peak shifts to a long wavelength side. When the measurement of glucose concentrations was conducted with lasers respectively having three wavelengths of 473 nm, 532 nm and 633 nm, the measurement with a laser having a wavelength of 532 nm had the highest sensitivity. In the case of a wavelength of 473 nm, DAP strongly absorbed light, whereas a polymer having a long π-electron conjugated length absorbed almost no light. In the case of a wavelength of 633 nm, DAP absorbed almost no light.

The results of the absorbance of the o-PD solution and the scattering intensity of the nanostructure at each wavelength are shown in Table 4.

TABLE 4

| | 473 nm | 532 nm | 633 nm |
|---|---|---|---|
| absorbance of the o-PD solution(dimer) | 0.056 | 0.017 | 0.007 |
| scattering intensity of the nanostructure [arb. u] | 0.03 | 0.05 | 0.06 |

FIG. 23 is a schematic diagram showing the progress state of the oxidative polymerization reaction of the o-PD by a focused laser light. As shown in this figure, the oxidative polymerization progresses due to light absorption of the dimer (DAP) immediately after focusing laser light, and when the oxidative polymerization further progresses and the nanostructure grows, the ratio of light absorption by the nanostructure increases. Accordingly, it can be assumed that light absorption by both of the dimer in the o-PD solution and the nanostructure is important for the method of the present invention. Therefore, as shown in Table 4 described above, it is considered that a green laser light having a wavelength of 532 nm at which light absorption by both of the dimer and the nanostructure occurs is most suitable to use for the detection of glucose.

4-5. Effects of Adding a Photosensitizer

In this experiment, the acceleration effects of an oxidative polymerization reaction caused by methylene blue, which is one of photosensitizers, were examined.

First, with reference to the energy diagram of a photosensitizer reaction shown in FIG. 24, the following discusses the mechanism in which oxidative polymerization proceeds by a focused laser light to form a coalescence in a nano-level. The ground state of oxygen molecule is a triplet state, and a singlet oxygen corresponding to an oxygen in an excited state is a useful oxidizing agent. The triplet state of dye molecules such as methylene blue has an excitation energy approximately equal to the energy difference between a singlet oxygen and a triplet oxygen. When the dye molecules are photoexcited, the transition to a triplet state is caused by intersystem crossing. When the dye in the triplet state collides with a triplet oxygen, exchange of electrons and energy takes place, and the triplet oxygen transits to a singlet oxygen simultaneously with the returning to the ground state of the dye. Oxidation by the singlet oxygen thus generated by photoexcitation is a typical mechanism of photooxidation reaction, and the dye used for generating a singlet oxygen is referred to as a photosensitizer.

In this experiment, using a He—Ne laser having a wavelength of 633 nm, which is hardly absorbed in a dimer (DAP) of o-PD, the photosensitization effect brought by methylene blue was examined. Specifically, methylene blue was dissolved in a citrate buffer such that a concentration of methylene blue became 200 μM, thereby adjusting a concentration of a methylene blue solution to 0.2 mM. Then, o-PD (4 mM) and the above methylene blue solution (0.2 mM) were mixed to obtain a mixed solution of o-PD (1 mM) and methylene blue (18.75 μM) (hereinafter, abbreviated as o-PD/blue solution).

The absorption spectrum of the o-PD/blue solution thus obtained is shown in FIG. 25. By adding methylene blue to the o-PD solution, in addition to the absorption instinct to o-PD, the absorption peak appeared on a longer wavelength side.

Next, 20 μL of each of glucose aqueous solutions (0 to 1 mM) and 20 μL of a GOD/HRP solution were mixed and allowed to stand at a constant temperature for one minute. 20 μL of the above o-PD/blue solution was added thereto, and 20 μL of the resulting mixed solution was added dropwise onto a base plate to measure the backscattered light intensity. The temporal variations of the backscattered light intensities obtained are shown in FIG. 26. Furthermore, a graph in which the peak absorbance with respect to each glucose concentration is plotted is shown in FIG. 27.

It can be seen from the above figure that the detection sensitivity of glucose improved by adding methylene blue, and the glucose concentrations of 0.25 to 1 mM were able to be quantified. This shows that the oxidation reaction by a singlet oxygen generated by light absorption is concerned with the formation of polymer by focused laser. Moreover, the above results show that the use of a photosensitizer such as methylene blue makes it possible to also apply to measurement systems using an inexpensive semiconductor laser (LD) having a wavelength of 650 nm.

In the above experiments, methylene blue was used as a photosensitizer, and in addition, a dimer (DAP) or a polymer of o-PD is also considered to act as a photosensitizer and promote oxidative polymerization of o-PD itself.

5. DETECTION OF ETHANOL

Here, ethanol was detected by the method of the present invention. The reaction formula of ethanol, AOD, o-PD and HRP is shown in the following.

[Chemical Formula 4]

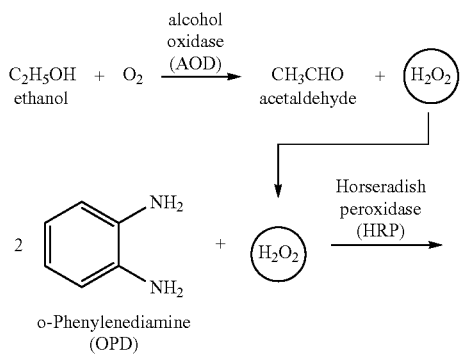

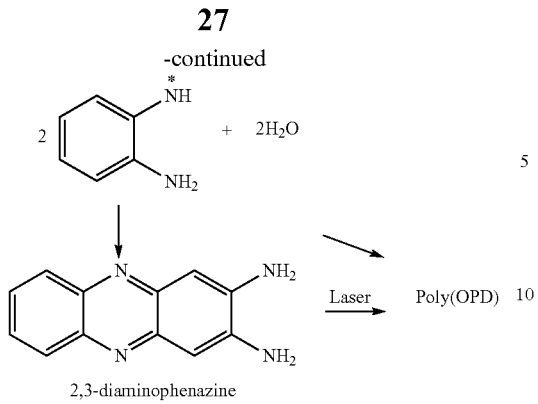

2,3-diaminophenazine

Ethanol was diluted with pure water to prepare five kinds of ethanols respectively having concentrations of 0 to 100 mM. AOD was dissolved in a citrate buffer to prepare an AOD solution such that the concentration became 100 units/mL.

Next, 20 μL of each ethanol (0 to 100 mM) prepared in the above manner, 10 μL of a HRP solution, and 10 μL of the AOD solution were mixed and allowed to stand at a constant temperature for one minute. 20 μL of an o-PD solution (1 mM) was added thereto, and 20 μL of the resulting mixed solution was added dropwise onto a base plate to measure the backscattered light intensity. The temporal variations of the backscattered light intensities obtained are shown in FIG. 28. A graph in which the peak time of the backscattered light intensity with respect to each ethanol concentration is plotted is shown in FIG. 29.

From these figures, according to the present invention, it was confirmed that ethanol can be detected in a concentration range of 10 to 100 mM.

6. APPLICATION TO IMMUNOSENSING

Here, using an IgG antibody-immobilized base plate on which a IgG antibody had been immobilized, a HRP-labeled anti-IgG antibody was bound thereto to detect the HRP-labeled anti-IgG antibody utilizing the oxidative polymerization reaction of o-PD by focused laser beam.

6-1. Preparation of a Sample Solution

A sample solution to be used for producing the IgG antibody-immobilized base plate was prepared in the following manner. First, an IgG antibody (ChromPure Human IgG, whole molecule, Jackson ImmunoReserch LABORATORIES, INC., 11.8 mg/mL) to be used as a receptor was dissolved in a HEPES buffer (10 mM, pH: 7.25) such that the concentration of the IgG antibody became 100 μg/mL. A HRP-labeled anti-IgG antibody (Rabbit polyclonal Secondary Antibody to Human IgG-H & L (HRP), pre-adsorbed, 0.5 mg/mL) as an antigen for detecting was dissolved in pure water to prepare an aqueous solution having a concentration of 10 ng/mL. The aqueous solution was diluted with pure water by repeating 10-fold dilutions to prepare 11 kinds of HRP-labeled anti-IgG antibody aqueous solutions respectively having concentrations of 10 fg/mL to 10 ng/mL.

Furthermore, in order to activate a carboxy group of the IgG antibody, a mixed solution of N-Hydroxysuccinimide (hereinafter, referred to as NHS) and 1-ethyl-3-(3-dimethylaminopropyl) carbodiimide hydrochloride (Dojindo) (hereinafter, referred to as WSC) was prepared in the following manner. First, NHS (Wako) was dissolved in a MES buffer (0.1 M, pH: 5.02) such that the concentration of NHS became 11 mg/mL. Furthermore, WSC (Dojindo) was dissolved in the above MES buffer such that the concentration of WSC became 4 mg/mL to prepare a mixed solution of NHS and WSC (hereinafter, abbreviated as NHS/WSC solution).

6-2. Preparation of an IgG Antibody-Immobilized Base Plate

Here, a cover glass for microscope having a smaller size than a size of a generally used commercially-available microplate was used as a base plate. In the ELISA method using the microplate, a sample solution, reagent and the like are each required at about 100 μL per well. However, the use of the above cover glass having a smaller size makes it possible to reduce the volume of the sample solution and the like. Therefore, a trace amount of test substance can be easily and sensitively detected.

First, a cover glass for microscope (size: 24 mm×36 mm, thickness: 0.12 to 0.17 mm, MATSUNAMI) that had been washed with a detergent was further washed with a plasma dry cleaner (PDC2102Z, Yamato Scientific Co., Ltd). The cover glass was immersed for 30 minutes in (3-Aminopropyl)triethoxysilane (98% or more, SIGMA-ALDRICH) diluted by 100-fold with ethanol, then washed with ethanol, and dried. Then, the cover glass was subjected to an aminosilane treatment by heating for two hours at 120° C. in a dry oven (DX31, yamato).

A silicon sheet having 9 to 12 holes with a diameter of 3.5 mm made using a punch was placed on the above cover glass to obtain a multiwell plate. Then, in order to activate a carboxyl group of the IgG antibody, 10 μL of a NHS/WSC solution and 990 μL of a IgG antibody solution were mixed, and 20 μL of the resulting mixed solution was added dropwise to each well and allowed to stand at a constant temperature for 30 minutes. Then, after washing and drying the base plate, 20 μL of a blocking reagent (ELISA ULTRA-BLOCK, AbD serotec) was added dropwise onto the base plate and allowed to stand at a constant temperature for 30 minutes to block unreacted amino groups. The IgG antibody-immobilized base plate thus prepared was stored in a cool dark place until the time of use.

6-3. ELISA Method

Part 1

A schematic diagram according to the present measurement method is shown in FIG. 30 (a).

An IgG antibody was immobilized on a glass plate, and the detection of a HRP-labeled anti-IgG antibody that specifically binds to the IgG antibody was performed. Specifically, 20 μL each of the HRP-labeled anti-IgG antibody solutions having different concentrations (10 fg/ml to 10 ng/ml) was added dropwise to the IgG antibody-immobilized base plate prepared in the manner as mentioned above, allowed to stand at a constant temperature for 30 minutes, then washed with a phosphate buffer solution, and dried.

Next, a mixed solution of o-PD (1 mM) and hydrogen peroxide (0.1 mM) was used as a reaction solution, and 20 μL of the reaction solution was added dropwise to each base plate, allowed to stand at a constant temperature for one minute, followed by focusing a laser light of 20 mW thereon to measure the change in backscattered light intensity. The results are shown in FIG. 30 (b). As shown in this figure, the higher the concentration of the HRP-labeled anti-IgG antibody solution dropped onto the base plate, the earlier the change in backscattered light intensity appeared.

FIG. 30 (c) is a graph showing the relationship between the time (in the vertical axis of the figure, indicated as "Predetermined time") obtained by measuring a time required for the backscattered light intensity to decrease once and increase again to the initial intensity and the concentration of the HRP-labeled anti-IgG antibody. It was confirmed from this figure that the above time has a good correlation when the concentration of the HRP labeled anti-IgG antibody is in a range of 10 pg/ml (50 fM) to 1 μg/ml (5 nM). This shows that, according to the method of the present invention, the concentration of the HRP-labeled antibody specifically bound to the test substance on the base plate can be quantified. That is, this shows that the method of the present invention can be used in the ELISA measurements such as the direct adsorption method and the sandwich method.

6-4. ELISA Method

Part 2

An anti-IgG antibody was detected by the competition method with a HRP-labeled anti-IgG antibody. A schematic diagram according to this measurement method is shown in FIG. 31(a).

20 μL of an anti-IgG antibody solution having each concentration (0 g/mL, 10 ng/mL, 100 ng/mL, 500 ng/mL, and 1 μg/mL) was added dropwise onto a IgG antibody-immobilized base plate prepared in the manner as mentioned above, and allowed to stand at a constant temperature for 30 minutes. The base plate was washed and then dried, and 20 μL of the HRP-labeled anti-IgG antibody solution (1 μg/mL) was added dropwise onto the base plate and allowed to stand at a constant temperature for 30 minutes. After washing and drying the base plate, a laser light was focused thereon to measure the backscattered light intensity. The results are shown in FIG. 31 (b). It was confirmed from this figure that the lower the concentration of the anti-IgG antibody, the earlier the change in backscattered light intensity appeared.

FIG. 31 (c) is a graph showing the relationship between the time (in the vertical axis of the figure, indicated as "Predetermined time") obtained by measuring a time required for the backscattered light intensity to decrease once and increase again to the initial intensity and the concentration of the HRP-labeled anti-IgG antibody. It can be seen from this figure that the anti-IgG antibody can be detected in a range of 10 ng/mL to 100 ng/mL. This shows that, according to the method of the present invention, the concentration of the antigen specifically bound to the test substance on the base plate can be quantified by allowing to compete with a HRP-labeled antibody. That is, this shows that the method of the present invention can be utilized in the ELISA measurement by the competitive method.

6-5. Method for Improving Detection Sensitivity in the ELISA Method

As described above, a base plate on which a test substance as well as receptors of an antibody and an antigen against the test substance are immobilized may be used in the ELISA method. However, since the surface of the base plate on which the antibody and the like are immobilized is not flat at a molecular level, nanostructures are hardly formed.

In view of the above, in order to eliminate the influence of immobilized antibody or the like on the base plate and to enhance the detection sensitivity of the measurement according to the method of the present invention, given is a method in which using a base plate 21 having an antibody existing region A where an antibody 23 exists and an antibody non-existing region B where an antibody 23 does not exist, the antibody non-existing region B is irradiated with a laser light, for example, as shown in FIG. 32. According to this method, polymers formed in the antibody existing region A penetrate also the antibody non-existing region B, and hence it is possible to directly irradiate the polymers with a laser light without requiring the aid of antibodies. Note that although an example in which the antibody 23 is immobilized on the base plate 21 is shown in FIG. 32, the present invention is not limited thereto. For example, the base plate may contain a group X substance existing region where at least one of group X substances including a test substance and a substance that exhibits a specific interaction with the test substance (for example, an antigen or an antibody), and a group X substance non-existing region where the above group X substances do not exist.

Specifically, for example as shown in FIG. 33, a doughnut-shaped porous support 22 may be provided on the base plate 21, and the antibody 23 may be immobilized (adsorbed) with the porous support 22. FIG. 33 shows a state in which a receptor such as an antibody or antigen is adsorbed to the porous support 22. An area (outside portion) on which the porous support 22 is provided is the antibody existing region A, and an area (central portion) on which no porous support is provided is the antibody non-existing region B. No particular restrictions are imposed on materials for the porous support 22 as long as the antibody 23 is easily immobilized, and in addition, the polymer formed in the antibody existing region easily penetrates the antibody non-existing region. As examples thereof, nitrocellulose, polyvinylidine fluoride, and the like can be given.

The porous support 22 may not touch the focused spot portion. For example as shown in FIG. 34, spacers 24 may be interposed between the porous support 22 and the base plate 21 such that the antibody does not exist at the focal point. As examples of the spacers 24, polymer fine particles can be given. Alternatively, the porous support 22 may be deformed in a convex shape, for example as shown in FIG. 35 (by providing a cavity at the focused spot position) such that the antibody does not exist at the focal point.

Alternatively, as shown in the experiments described in the following 7-3, a base plate on which an antibody exists and a base plate on which an antibody does not exist are stacked as shown in FIG. 40, and the irradiation of light may be performed through the base plate on which an antibody does not exist. According to this method, it has been demonstrated that since there is no antibody at the focal point, the test substance can be quantitatively measured with high sensitivity. The details of the experimental methods and results will be described in the following 7-3. Note that although an example in which the antibody 25 is immobilized on the cover glass 17 used as a base plate is shown in FIG. 40, the present invention is not limited thereto. For example, a base plate where, in addition to the antibody, at least one of substance in a group X consisting of a test substance and a substance having a specific interaction with the test substance (for example, an antigen) exists may be used.

7. APPLICATION TO IMMUNOSENSING

Part 2

Generally, reagent kits containing a microplate on which an antibody against a detection target substance is immobilized, an enzyme-labeled antibody (secondary antibody), a solution required for dilution or blocking or the like, a chromogenic substrate to produce a color or a fluorescent substance by reacting with an enzyme, and the like are often used in the ELISA method. In the following, the comparative experiments of the conventional absorbance measurement method and the backscattered light intensity measurement method of the present invention were performed using commercially-available ELISA kits.

7-1. Measurement of Specific Binding of IgG and HRP-Labeled Anti-IgG Antibody by ELISA Method In this experiment, an IgG antibody was used as a test substance. Furthermore, a HRP-labeled anti-IgG antibody (secondary antibody), a blocking solution, a washing solution, and the protocol in each step included in Protein Detector ELISA Kit, Anti-Human of KPL Inc. were used in this experiment.
(1) Experimental Method
  100 µL of the IgG antibody (14.7 mg/L) was added dropwise to each well in a microplate (Nunc, Maxiplate), allowed to stand at room temperature for three hours, and then washed to be solid-phased. Specifically, 300 µL of the blocking solution was added dropwise to each well, allowed to stand at room temperature for five minutes, and then washed to conduct blocking. Next, 100 µL of the HRP-labeled anti-IgG antibody diluted so as to have each concentration was added dropwise to each well, allowed to stand at room temperature for one hour, and then washed to prepare a IgG antibody solid phase base plate.
  Next, as a reaction solution, 100 µL of a mixed solution of o-PD of 2 mM and a citrate buffer solution containing hydrogen peroxide of 10 mM was added dropwise to each well and allowed to stand at room temperature for one hour.
(2) Measurement According to the Method of the Present Invention
  10 µL of the solution after left to stand obtained in the above manner was collected from each well, and added dropwise to a glass plate prepared separately. Then, laser (wavelength: 532 nm, intensity: 8 mW) was focused on the solid-liquid interface between the above glass plate and the above solution using a 60× objective lens to measure the change in backscattered light intensity.
(3) Measurement According to the Conventional Absorbance Measurement Method
  The absorbance at a wavelength of 405 nm in each well was measured using a microplate reader (Corona Electric, SH-1000).
(4) Measurement Results and Discussion
  These results are shown in FIG. 36 (the conventional method) and FIG. 37 (the method of the present invention). Specifically, FIG. 36 is a graph showing the relationship between the absorbance and the concentration of the HRP-labeled anti-IgG antibody. FIG. 37 is a graph showing the relationship between the time when the first peak of the backscattered light intensity appeared (in the vertical axis of the figure, indicated as "Peak time") and the concentration of the HRP-labeled anti-IgG antibody. Comparing these figures, a clear difference between both was observed at an extremely trace amount level of 100 pg/mL or less of the HRP-labeled anti-IgG antibody concentration. Therefore, it was confirmed that according to the method of the present invention, the quantitative measurement for an extremely low concentration of, for example, 10 pg/mL or more can be conducted, which was difficult in the conventional absorbance method.

7-2. Measurement of C-Reactive Protein by the Sandwich ELISA Method

In this experiment, C-reactive protein (CRP) was used as a test substance. CRP is a protein that appears in blood when inflammatory response or destruction of tissues occurs in the body, and serves as an index of diseases such as infections, malignancies, myocardial infarctions, and the like. In this experiment, CRP was measured using a common sandwich method. Specifically, the measurement was carried out using an antibody solid-phased microplate, a HRP-labeled secondary antibody, a dilution solution, the protocol of each step included in High Sensitivity C-reactive Protein Enzyme Immunoassay Test Kit of Biocheck Corporation.
(1) Experimental Method
  First, 10 µL of a CRP solution having an adjusted concentration was added dropwise to each well of the microplate on which an anti-CRP antibody had been solid-phased. Then, 100 µL of the HRP-labeled secondary antibody was added dropwise to each well and allowed to stand at room temperature for 45 minutes.
(2) Measurement by the Method of the Present Invention
  As a reaction solution, 100 µL of a mixed solution of o-PD of 2 mM and a citrate buffer solution containing hydrogen peroxide of 10 mM was added dropwise to each well and allowed to stand at room temperature for one hour.
  10 µL of the solution after left to stand obtained in the above manner was collected from each well, and added dropwise to a glass plate prepared separately. Then, laser (wavelength: 532 nm, intensity: 9.7 mW) was focused on the solid-liquid interface between the above glass plate and the above solution using a 60× objective lens to measure the change in backscattered light intensity.
(3) Measurement of the Conventional Absorbance Measurement Method
  As a reaction solution, 100 µL of a reaction solution [a mixed solution of 3,3',5,5'-tetramethylbenzidine (TMB) and hydrogen peroxide] included in the above kit used in this experiment was added dropwise to each well and allowed to stand at room temperature for one hour, and then, 100 µL of a reaction stop solution included in the above kit was added dropwise to each well. The absorbance at a wavelength of 405 nm in each well was measured using a microplate reader (Corona Electric, SH-1000).
(4) Measurement Results and Discussion
  These results are shown in FIG. 38 (the conventional method) and FIG. 39 (the method of the present invention). Specifically, FIG. 38 is a graph showing the relationship between the absorbance and the CRP concentration. FIG. 39 is a graph showing the relationship between the time (in the vertical axis of the figure, indicated as "Predetermined time") obtained by measuring a time required for the backscattered light intensity to decrease once and increase again to the initial intensity and the CRP concentration. Although the strict measurement sensitivity depends on the ELISA kit used, it was confirmed that according to the method of the present invention, the quantitative measurement of CRP having an extremely low concentrations of, for example, 500 pg/mL or more can be conducted, which was difficult in the conventional absorbance method.

7-3. Measurement by the ELISA Method Using an IgG Antibody Solid-Phased Cover Glass In this experiment, an IgG antibody was used as a test substance, and a smaller cover glass in size than a microplate was used as a base plate in order to measure a trace amount. A HRP-labeled anti-IgG antibody (secondary antibody), a blocking solution, a washing solution, and the protocol of each step included in Protein Detector ELISA Kit, Anti-Human of KPL Inc. were used in this experiment.

(1) Experimental Method

The measurement procedure of this experiment is described with reference to FIG. 40. First, a polystyrene solution (solvent: xylene, concentration: 10 wt %) was added dropwise onto a cover glass for microscope 17 (size: 24 mm×36 mm, thickness: 0.12 to 0.17 mm, MATSUNAMI) to prepare a polystyrene thin film by spin coating. Next, a silicon sheet 15 (thickness: 0.2 mm, Asone) having holes with a diameter of 3 mm are brought into close contact with the prepared polystyrene thin film to produce wells. Then, 10 µL of a IgG antibody 25 (14.7 mg/L) was added dropwise to each well and allowed to stand at room temperature for three hours, followed by washing. Next, 10 µL of the blocking solution was added dropwise to each well and allowed to stand at room temperature for five minutes, followed by washing to perform blocking, thereby obtaining a IgG antibody solid-phased base plate (see (1) of FIG. 40).

To the wells of the IgG antibody solid-phased base plate obtained in this manner, 10 µL of a HRP-labeled secondary antibody diluted so as to have each concentration was added dropwise and allowed to stand at room temperature for one hour, followed by washing. Then, as a reaction solution, 10 µL of a mixed solution of o-PD of 2 mM and a citrate buffer solution containing hydrogen peroxide of 10 mM was added dropwise to each well and allowed to stand at room temperature for one hour (see (2) of FIG. 40). These wells include a polymerized substance-containing solution 26.

Next, the base plate 27 after left to stand was turned over as shown in (3) of FIG. 40, silicone rubber sheets having a thickness of 1 mm were adhered as a spacer 24 at both ends of the base plate 27 (see (5) of FIG. 40), and the same cover glass 28 (clean base plate without a polystyrene thin film) as one used in preparing the above base plate was stacked thereon. Next, as shown in (4) of FIG. 40, laser (wavelength: 532 nm, intensity: 2.6 mW) was focused on the solid-liquid interface between the cover glass 28 and the polymerized substance-containing solution 26 using a 60× objective lens to measure the change in backscattered light intensity. That is, according to this experimental method, as shown in (5) of FIG. 40, laser is focused on the solid-liquid interface between the clean cover glass 28 on which antibodies are not solid-phased and the polymerized substance-containing solution 26, and therefore, the nanostructures can be formed.

(2) Measurement Results and Discussion

The results obtained are shown in FIG. 41. FIG. 41 is a graph showing the relationship between the time when the first peak of the backscattered light intensity appeared (in the vertical axis of the figure, indicated as "Peak time") and the concentration of the HRP-labeled anti-IgG antibody (secondary antibody). It was found that when using the method in which the antibody solid-phased base plate and the clean base plate are stacked and laser is focused from the clean base plate side as in this experiment, an anti-IgG antibody of 1 ng/mL or more can be measured with high reproducibility.

8. CONCLUSIONS

When the green laser light is focused on the o-PD solution as described above, the oxidative polymerization reaction progresses at the focal point on the base plate, and the backscattered light intensity temporally changes along with the growth of nano-sized polymers formed by the reaction. It was confirmed from the SEM observation images that the oxidative polymerization reaction was accelerated by the reaction of peroxidase enzyme such as HRP, thereby increasing the formation rate of polymers. The method of the present invention utilizes these phenomena, and the glucose concentrations in a range of 100 nM to 1 mM were able to be quantified with high sensitivity according to the method of the present invention. It was also found from the examination of the laser wavelength dependence in the detection of glucose that a green laser light having a wavelength of 532 nm is suitable for the detection of glucose. Furthermore, it was strongly suggested from the relationship between the wavelength dependence of laser light, the absorption spectra of the o-PD solution, and the backscattered light intensity spectra of the polymer that light absorption by both of DAP (dimer) in the o-PD solution and the polymers formed at the focal point is important in the detection method of the present invention. Additionally, it was possible to quantitatively detect ethanol by the method of the present invention.

Furthermore, the method of the present invention is also applicable to immunoassays. As the result of preparing of the IgG antibody-immobilized base plate and measuring it by the ELISA method, it was possible to detect HRP-labeled anti-IgG antibodies of 10 pg/mL to 10 µg/mL.

In applications to immunoassays, the detection sensitivity of HRP-labeled anti-IgG antibodies can be further improved, for example, by adequately controlling a concentration of a sample solution containing a test substance, an immobilization method of antibodies on a base plate, and the like. Furthermore, a portable as well as rapid and highly sensitive ELISA measurement system can be realized by downsizing measurement apparatuses. The method of the present invention can be also applied to, for example, multi-sensor chips in which a plurality of enzymes are immobilized on a single base plate. Accordingly, the technique of the present invention is extremely useful for the development of a small, inexpensive and simple biosensing system capable of detecting an extremely trace amount of test substance.

DESCRIPTION OF REFERENCE NUMERALS

1 laser beam
2 beam expander
3 ND filter
4 mechanical shutter
5 inverted microscope
6 half mirror
7 objective lens
8 stage
9 base plate
10 nanostructure
11 coupler
12 optical fiber
13 photomultiplier tube
14 expansion board for storing data
15 silicon sheet 16 solution
17 cover glass
21 base plate
22 porous support
23 antibody
24 spacer
25 antibody (IgG)
26 polymerized substance-containing solution
27 antibody solid phase base plate

The invention claimed is:

1. A method for measuring a concentration of a test substance that is detectable by an antigen-antibody interaction, the method comprising the steps of:
   (1) preparing a base plate having a region A where an antibody is immobilized on the base plate, and a region B where no antibody and no antigen is immobilized on the base plate,
   (2) modifying the antibody with an oxidoreductase;
   (3) adding a test substance comprising an antigen to the base plate and allowing an antigen-antibody interaction to proceed in the region A;
   (4) adding a peroxide and o-phenylenediamine to the test substance on the base plate to produce a solution of diaminophenazine wherein the solution of diaminophenazine exists in region A and region B;
   (5) irradiating region B with light, wherein the light is focused on the interface between a light-transmitting base and the solution in the region B, and allowing the diaminophenazine to aggregate in a focal spot on the base plate to obtain a polymer that scatters light;
   (6) recording the temporal variation of the intensity of scattered light generated from the focal spot of the light, based on the phase difference of two lights, wherein a first light is reflected at the interface between the base and the polymer, and a second light is reflected at the interface between the polymer and the solution containing the diaminophenazine; and
   (7) determining the concentration of the test substance from the temporal variation.

2. The method for measuring a concentration of a test substance according to claim 1,
   wherein a support having a plurality of pores is provided on the plate and the test substance and the antibody is immobilized within each pore of the support.

3. A method for measuring a concentration of a test substance that is detectable by an antigen-antibody interaction, the method comprising the steps of:
   (1) preparing a base plate having a region A where an antigen is immobilized on the base plate, and a region B where no antibody and no antigen is immobilized on the base plate;
   (2) modifying the antigen with an oxidoreductase;
   (3) adding a test substance comprising an antibody to the base plate and allowing an antigen-antibody interaction to proceed in the region A;
   (4) adding a peroxide and o-phenylenediamine to the test substance on the base plate to produce a solution of diaminophenazine wherein the solution of diaminophenazine exists in region A and region B;
   (5) irradiating region B with light, wherein the light is focused on the interface between a light-transmitting base and the solution in the region B, and allowing the diaminophenazine to aggregate in a focal spot on the base plate to obtain a polymer that scatters light;
   (6) recording the temporal variation of the intensity of scattered light generated from the focal spot of the light, based on the phase difference of two lights, wherein a first light is reflected at the interface between the base and the polymer, and a second light is reflected at the interface between the polymer and the solution containing the diaminophenazine; and
   (7) determining the concentration of the test substance from the temporal variation.

4. The method for measuring a concentration of a test substance according to claim 3,
   wherein a support having a plurality of pores is provided on the plate and the test substance and the antigen is immobilized within each pore of the support.

* * * * *